United States Patent [19]

Sager et al.

[11] Patent Number: 5,470,970

[45] Date of Patent: Nov. 28, 1995

[54] MASPIN, A SERPIN WITH TUMOR SUPPRESING ACTIVITY

[75] Inventors: Ruth Sager, Brookline, Mass.; Anthony Anisowicz, West Newton, Mass.; Zhiqiang Zou, Gaithersburg, Md.

[73] Assignee: Dana-Farber Cancer Institute, Inc., Boston, Mass.

[21] Appl. No.: 121,714

[22] Filed: Sep. 1, 1993

Related U.S. Application Data

[63] Continuation-in-part of Ser. No. 938,823, Sep. 1, 1992, abandoned, which is a continuation-in-part of Ser. No. 844,296, Feb. 28, 1992, abandoned, which is a continuation-in-part of Ser. No. 662,216, Feb. 28, 1991, abandoned.

[51] Int. Cl.$^6$ .............................. C12N 1/21; C12N 5/10; C12N 15/15; C07K 14/47
[52] U.S. Cl. ................. 536/23.5; 536/24.31; 435/320.1; 435/252.3; 435/240.1; 530/350; 530/828; 930/250; 930/10; 935/9
[58] Field of Search ............................. 435/6, 69.1, 69.2, 435/320.1; 536/23.1, 23.2; 530/350, 828; 930/250

[56] References Cited

U.S. PATENT DOCUMENTS 4,888,278  12/1989  Singer et al. ................................ 435/6

OTHER PUBLICATIONS

Z. Zou et al. Science 263:526 Jan. 28, 1994.
A. C. Webb et al. J. Exp Med 166:77–94 1987.
Band and Sager, Distinctive Traits of Normal and Tumor–derived Human Mammary Epithelial Cells Expressed in a Medium that Supports Long–term . . . Growth of Both Cell Types, Proc. Natl. Acad. Sci. USA 86:1249–1253, 1989.
Band et al., Tumor Progression in Four Mammary Epithelial Cell Lines Derived from the Same Patient, Cancer Research, 50:7351–7357, 1990.
Band et al., A Newly Established Metastatic Breast Tumor Cell Line with Integrated Amplified Copies of ERBB2 and Double Minute Chromosomes, Genes, Chromosomes & Cancer 1:48–58, 1989.
Baumann et al., Crystal Structure of Cleaved Human $\alpha_1$–Antichymotrypsin at 2–7 ÅResolution and its Comparison with Other Serpins, J. Mol. Biol. 218:595–606, 1991.
Baylin et al., Hypermethylation of the 5' Region of the Calcitonin Gene is a Property of Human Lymphoid and Acute Myloid Malignancies, Blood 70:412–417, 1987.
Calabretta et al., Molecular Cloning of the cDNA for a Growth Factor–inducible Gene with Strong Homology to S–100, a Calcium–binding Protein, J. Biol. Chem. 261:12628–12632, 1986.
Carr et al., The Tumorigenicity of 5–azacytidine in the Male Fischer Rat, Carcinogenesis 5:1583–1590, 1984.
Cattaneo et al., Altered Ratios of Measles Virus Transcripts in Diseased Human Brains, Virology 160:523–526, 1987.
Cowan et al., Similar Biochemical Changes Associated with Multidrug Resistance in Human Breast Cancer Cells and Carcingen–induced Resistance to Xenobiotics in Rats, Proc. Natl. Acad. Sci. USA 83:9328–9322, 1986.
El–Deiry et al., High Expression of the DNA Methyltransferase Gene Characterizes Human Neoplastic Cells and Progession Stages of Colon Cancer, Proc. Natal. Acad. Sci. USA 88:3470–3474, 1991.
Friedmann, Gene Therapy, Therapy for Genetic Disease, pp. 107–121.

(List continued on next page.)

*Primary Examiner*—Garnette D. Draper
*Assistant Examiner*—Lorraine M. Spector
*Attorney, Agent, or Firm*—Fish & Richardson

[57] ABSTRACT

An isolated DNA encoding a polypeptide substantially identical to maspin (SEQ ID NO:1); a substantially purified preparation of maspin; an antibody specific for maspin; and use of such DNAs and antibodies in diagnostic, screening, and therapeutic methods.

17 Claims, 9 Drawing Sheets

OTHER PUBLICATIONS

Gibbs et al., Characterization of the Human spr2 Promoter: Induction after UV Irradiation or TPA Treatment and Regulation During Differentiation of . . . Primary Keratinocytes, Nucleic Acids Res. 18:4401–4407, 1990.

Harrison et al., Azacytidine–Induced Tumorigenesis of CHEF/18 Cells: Correlated DNA Methylation and Chromosome Changes, Proc. Natl. Acad. Sci. USA 80:6606–6610, 1983.

Hendrix et al., A Simple Quantitative Assay for Studying the Invasive Potential of High and Low Human Metastatic Varients, Cancer Letters 38:137–147, 1987.

Huber et al., Implication of the Three–Dimensional Structure of $\alpha_1$–Antitrypsin for Structure and Function of Serpins, Biochemistry 28:8951–8966, 1989.

Jones and Buckley, The Role of DNA Methylation in Cancer, Advances in Cancer Research 54:1–23, 1990.

Kligman and Hilt, The S100 Protein Family, Trends in Biochemical Sciences 13:437–443, 1988.

Lee et al., Down–regulation of a Member of the S100 Gene Family in Mammary Carcinoma Cells and Reexpression by Azadeoxycytidine Treatment, Proc. Natl. Acad. Sci. USA 89:2504–2508, 1992.

Lee et al., Positive Selection of Candidate Tumor–Suppressor Genes by Subtractive Hybridization, Proc. Natl. Acad. Sci. USA 88:2825–2829, 1991.

Lee et al., Isolation and Characterization of Eight Tumor Necrosis Factor–Induced Gene Sequences from Human Fibroblasts, Molecular and Cellular Biology 10:1982–1988, 1990.

Lersch and Fuchs, Sequence and Expression of a Type II Keratin, K5, in Human Epidermal Cells, Molecular and Cellular Biology 8:486–493, 1988.

Liotta and Stetler–Stevenson, Tumor Invasion and Metastasis: An Imbalance of Positive and Negative Regulation, Cancer Reserach(Suppl.) 51:5054s–5059s, 1991.

Lobermann et al., Human $\alpha_1$–Proteinase Inhibitor, J. Mol. Biol. 177:531–556, 1984.

Moscow et al., Expression of Anionic Glutathione–S–transferase and P–Glycoprotein Genes in Human Tissues and Tumors, Cancer Research 49:1422–1428, 1989.

Mottonen et al., Structural Basis of Latency in Plasminogen Activator Inhibitor–1, Nature 355:270–273, 1992.

Price et al., Tumorigenicity and Metastasis of Human Breast Carcinoma Cell Lines in Nude Mice, Cancer Research 50:717–721, 1990.

Remond–O'Donnell et al., Sequence and Molecular Characterization of Human Monocyte/Neutrophil Elastase Inhibitor, Proc. Natl. Acad. Sci. USA 89:5635–5639, 1992.

Sager et al., Identification by Differential Display of Alpha 6 Integrin as a Candidate Tumor Suppressor Gene, FASEB J. 7:964–970, 1993.

Sager, Tumor Suppressor Genes: The Puzzle and the Promise, Science 246:1406–1412, 1989.

Saheki et al., Primary Structure of the Human Elafin Precursor Preproelafin Deduced from the Nucleotide Sequence . . . Repetitive Sequences in the Prosegment, Biochem. & Biophys. Research Comm. 185:240–245, 1992.

Stein et al., Crystal Structure of Ovalbumin as a Model for the Reactive Centre of Serpins, Nature 347:99–102, 1990.

Testa and Quigley, The Role of Urokinase–type Plasminogen Activator in Agressive Tumor Cell Behavior, Cancer and Metastasis Reviews 9:353–367, 1990.

Tomasetto et al., Specificity of Gap Junction Communication Among Human Mammary Cells and Connexin Transfectants in Culture, J. Cell Biol. 122:157–167, 1993.

Trask et al., Keratins as Markers that Distinguish Normal and Tumor–derived Mammary Epithelial Cells, Proc. Natl. Acad. Sci. USA 87:2319–2323, 1990.

Travis et al., Serpins: Structure and Mechanism of Action, Biological Chemistry Hoppe–Seyler 371(Suppl.): 3–11, 1990.

Tsunemi et al., Synthesis and Structure–Activity Relationships of Elafin, an Elastase–Specific Inhibitor, Biochemical and Biophysical Research Communications 185:967–973, 1992.

Wiedow et al., Elafin: An Elastase–specific Inhibitor of Human Skin, J. Biol. Chem. 265:14791–14795, 1990.

Wright et al., Crystal Structure of Plakalbumin, a Proteolytically Nicked Form of Ovalbumin, J. Mol. Biol. 213:513–528, 1990.

Yaswen et al., Down–regulation of a Calmodulin–related Gene During Transformation of Human Mammary Epithelial Cells, Proc. Natl. Acad. Sci. USA 87:7360–7364, 1990 numerous passages eligble.

Zhang and Nicholson, Sequence and Tissue Distribution of a Second Protein of Hepatic Gap Junctions, Cx26, As Deduced from its cDNA, J. Cell Biol. 109:3391–3401, 1989.

```
GGCACGAGTT GTGCTCCTCG CTTGCCTGTT CCTTTTCCAC GCATTTTCCA GGATAACTGT        60

GACTCCAGGC CCGCA ATG GAT GCC CTG CAA CTA GCA AAT TCG GCT TTT GCC       111
                Met Asp Ala Leu Gln Leu Ala Asn Ser Ala Phe Ala

GTT GAT CTG TTC AAA CAA CTA TGT GAA AAG GAG CCA CTG GGC AAT GTC        159
Val Asp Leu Phe Lys Gln Leu Cys Glu Lys Glu Pro Leu Gly Asn Val

CTC TTC TCT CCA ATC TGT CTC TCC ACC TCT CTG TCA CTT GCT CAA GTG        207
Leu Phe Ser Pro Ile Cys Leu Ser Thr Ser Leu Ser Leu Ala Gln Val

GGT GCT AAA GGT GAC ACT GCA AAT GAA ATT GGA CAG GTT CTT CAT TTT        255
Gly Ala Lys Gly Asp Thr Ala Asn Glu Ile Gly Gln Val Leu His Phe

GAA AAT GTC AAA GAT ATA CCC TTT GGA TTT CAA ACA GTA ACA TCG GAT        303
Glu Asn Val Lys Asp Ile Pro Phe Gly Phe Gln Thr Val Thr Ser Asp

GTA AAC AAA CTT AGT TCC TTT TAC TCA CTG AAA CTA ATC AAG CGG CTC        351
Val Asn Lys Leu Ser Ser Phe Tyr Ser Leu Lys Leu Ile Lys Arg Leu

TAC GTA GAC AAA TCT CTG AAT CTT TCT ACA GAG TTC ATC AGC TCT ACG        399
Tyr Val Asp Lys Ser Leu Asn Leu Ser Thr Glu Phe Ile Ser Ser Thr

AAG AGA CCC TAT GCA AAG GAA TTG GAA ACT GTT GAC TTC AAA GAT AAA        447
Lys Arg Pro Tyr Ala Lys Glu Leu Glu Thr Val Asp Phe Lys Asp Lys

TTG GAA GAA ACG AAA GGT CAG ATC AAC AAC TCA ATT AAG GAT CTC ACA        495
Leu Glu Glu Thr Lys Gly Gln Ile Asn Asn Ser Ile Lys Asp Leu Thr

GAT GGC CAC TTT GAG AAC ATT TTA GCT GAC AAC AGT GTG AAC GAC CAG        543
Asp Gly His Phe Glu Asn Ile Leu Ala Asp Asn Ser Val Asn Asp Gln

ACC AAA ATC CTT GTG GTT AAT GCT GCC TAC TTT GTT GGC AAG TGG ATG        591
Thr Lys Ile Leu Val Val Asn Ala Ala Tyr Phe Val Gly Lys Trp Met

AAG AAA TTT CCT GAA TCA GAA ACA AAA GAA TGT CCT TTC AGA CTC AAC        639
Lys Lys Phe Pro Glu Ser Glu Thr Lys Glu Cys Pro Phe Arg Leu Asn

AAG ACA GAC ACC AAA CCA GTG CAG ATG ATG AAC ATG GAG GCC ACG TTC        687
Lys Thr Asp Thr Lys Pro Val Gln Met Met Asn Met Glu Ala Thr Phe
```

FIG. 3-1

```
TGT ATG GGA AAC ATT GAC AGT ATC AAT TGT AAG ATC ATA GAG CTT CCT      735
Cys Met Gly Asn Ile Asp Ser Ile Asn Cys Lys Ile Ile Glu Leu Pro

TTT CAA AAT AAG CAT CTC AGC ATG TTC ATC CTA CTA CCC AAG GAT GTG      783
Phe Gln Asn Lys His Leu Ser Met Phe Ile Leu Leu Pro Lys Asp Val

GAG GAT GAG TCC ACA GGC TTG GAG AAG ATT GAA AAA CAA CTC AAC TCA      831
Glu Asp Glu Ser Thr Gly Leu Glu Lys Ile Glu Lys Gln Leu Asn Ser

GAG TCA CTG TCA CAG TGG ACT AAT CCC AGC ACC ATG GCC AAT GCC AAG      879
Glu Ser Leu Ser Gln Trp Thr Asn Pro Ser Thr Met Ala Asn Ala Lys

GTC AAA CTC TCC ATT CCA AAA TTT AAG GTG GAA AAG ATG ATT GAT CCC      927
Val Lys Leu Ser Ile Pro Lys Phe Lys Val Glu Lys Met Ile Asp Pro

AAG GCT TGT CTG GAA AAT CTA GGG CTG AAA CAT ATC TTC AGT GAA GAC      975
Lys Ala Cys Leu Glu Asn Leu Gly Leu Lys His Ile Phe Ser Glu Asp

ACA TCT GAT TTC TCT GGA ATG TCA GAG ACC AAG GGA GTG GCC CTA TCA     1023
Thr Ser Asp Phe Ser Gly Met Ser Glu Thr Lys Gly Val Ala Leu Ser

AAT GTT ATC CAC AAA GTG TGC TTA GAA ATA ACT GAA GAT GGT GGG GAT     1071
Asn Val Ile His Lys Val Cys Leu Glu Ile Thr Glu Asp Gly Gly Asp

TCC ATA GAG GTG CCA GGA GCA CGG ATC CTG CAG CAC AAG GAT GAA TTG     1119
Ser Ile Glu Val Pro Gly Ala Arg Ile Leu Gln His Lys Asp Glu Leu

AAT GCT GAC CAT CCC TTT ATT TAC ATC ATC AGG CAC AAC AAA ACT CGA     1167
Asn Ala Asp His Pro Phe Ile Tyr Ile Ile Arg His Asn Lys Thr Arg

AAC ATC ATT TTC TTT GGC AAA TTC TGT TCT CCT TAAGTGGCAT AGCCCATGTT   1220
Asn Ile Ile Phe Phe Gly Lys Phe Cys Ser Pro

AAGTCCTCCC TGACTTTTCT GTGGATGCCG ATTTCTGTAA ACTCTGCATC CAGAGATTCA   1280
TTTTCTAGAT ACAATAAATT GCTAATGTTG CTGGATCAGG AAGCCGCCAG TACTTGTCAT   1340
ATGTAGCCTT CACACAGATA GACCTTTTTT TTTTTCCAAT TCTATCTTTT GTTTCCTTTT   1400
TTCCCATAAG ACAATGACAT ACGCTTTTAA TGAAAAGGAA TCACGTTAGA GGAAAAATAT   1460
TTATTCATTA TTTGTCAAAT TGTCCGGGGT AGTTGGCAGA AATACAGTCT TCCACAAAGA   1520
```

FIG. 3-2

```
AAATTCCTAT AAGGAAGATT TGGAAGCTCT TCTTCCCAGC ACTATGCTTT CCTTCTTTGG 1580
GATAGAGAAT GTTCCAGACA TTCTCGCTTC CCTGAAAGAC TGAAGAAAGT GTAGTGCATG 1640
GGACCCACGA AACTGCCCTG GCTCCAGTGA AACTTGGGCA CATGCTCAGG CTACTATAGG 1700
TCCAGAAGTC CTTATGTTAA GCCCTGGCAG GCAGGTGTTT ATTAAAATTC TGAATTTTGG 1760
GGATTTTCAA AAGATAATAT TTTACATACA CTGTATGTTA TAGAACTTCA TGGATCAGAT 1820
CTGGGGCAGC AACCTATAAA TCAACACCTT AATATGCTGC AACAAAATGT AGAATATTCA 1880
GACAAAATGG ATACATAAAG ACTAAGTAGC CCATAAGGGG TCAAAATTTG CTGCCAAATG 1940
CGTATGCCAC CAACTTACAA AAACACTTCG TTCGCAGAGC TTTTCAGATT GTGGAATGTT 2000
GGATAAGGAA TTATAGACCT CTAGTAGCTG AAATGCAAGA CCCCAAGAGG AAGTTCAGAT 2060
CTTAATATAA ATTCACTTTC ATTTTTGATA GCTGTCCCAT CTGGTCATGT GGTTGGCACT 2120
AGACTGGTGG CAGGGGCTTC TAGCTGACTC GCACAGGGAT TCTCACAATA GCCGATATCA 2180
GAATTTGTGT TGAAGGAACT TGTCTCTTCA TCTAATATGA TAGCGGGAAA AGGAGAGGAA 2240
ACTACTGCCT TTAGAAAATA TAAGTAAAGT GATTAAAGTG CTCACGTTAC CTTGACACAT 2300
AGTTTTTCAG TCTATGGGTT TAGTTACTTT AGATGGCAAG CATGTAACTT ATATTAATAG 2360
TAATTTGTAA AGTTGGGTGG ATAAGCTATC CCTGTTGCCG GTTCATGGAT TACTTCTCTA 2420
TAAAAAATAT ATATTTACCA AAAAATTTTG TGACATTCCT TCTCCCATCT CTTCCTTGAC 2480
ATGCATTGTA AATAGGTTCT TCTTGTTCTG AGATTCAATA TTGAATTTCT CCTATGCTAT 2540
TGACAATAAA ATATTATTGA ACTACCAAAA AAAAAAAAAA AAAA            2584
```

```
serapin    DIEDESTGLE KIEKQLTLEK LREWTKPENL YLAEVNVHLP RFKLEESVDL TSHIARLGVQ DLFNRGKADL SGMSGARDIF
ei         DIEDESTGLK KIEEQLTLEK LHEWTKPENL DFIEVNVSLP RFKLEESVTL NSDIARLGVQ DLFNSSKADL SGMSGARDIF
maspin     DVEDESTGLE KIEKQINSES LSQWINPSTM ANAKVKLSIP KFKVEKMIDP KACLENLGLK KFKVEKMIDP HIFSEDTSDF SGMSETKGVA
pai2       EIADVSTGLE ILESEITVDK LNKWTSKDKM AEDEVEVYIP QFKLEEHYEL RSIRSMGME DAFNKGRANF SGMSERNDIF
pai1       EKE...VPIS ALTNILSAQL ISHWK...GNM TRLPRLLVLP KFSLETEVDL RKPLENLGMT DMFRQFQADF TSLSDQEPLH
at         PDE...GKIQ HLENELTHDI ITKFL...ENE DRRSASLHLP KLSITGTVDL KSVIGQLGIT KVFSN.GADL SGVTEEAPLK
ovalbu     EV.....SGLE QLESIINFEK LTEWTSSNVM EERKIKVVLP RMKMEEKYNL TSVLMAMGIT DVFSSS.ANL SGISSAESLK 468
serapin    VSKIIHKSFV DLNEEGTEAA AATAGTIMLA MLMPEENFNA DHPFLFFIRH NPSANILFLG RFSSFX...
ei         ISKIVHKSFV EVNEEGTEAA AATAGIATFC MLMPEENFTA DHPFLFFIRH NSSGSILFLG RFSSFX...
maspin     LSNVIHKVCL EITEDGDSI  EVPGA....R ILQHKDELNA DHPFIYIIRH NKTRNILFFG KFCSPX...
pai2       LSEVFLQAMV DVNEEGTEAA AGTGGVMTGR TGHGPQEVA  DHPFLFLIMH DRPLFLFVRH NFTGTVLFMG RFCSP....
pai1       VAQAIQKVKI EVNESGTVAS SSTAVIVSAR MA..PEEIIM DRPLFVVRH NKPVFLMIE  QNTKSPLFMG QVMEP....
at         ISKAVHKAVL TIDEKGTEAA GAMFLEAIPM SI...PPEVKF NKPVFLMIE  QNTKSPLFMG KVVNPTQK...
ovalbu     ISQAVHAAHA EINEAGREVV GSAEAGVDAA SV..SEEFRA DHPFLFCIKH IATNAVLFFG RCVEP....
                                              AbS3A
```

FIG. 4-2

FIG. 6A   FIG. 6B   FIG. 6C
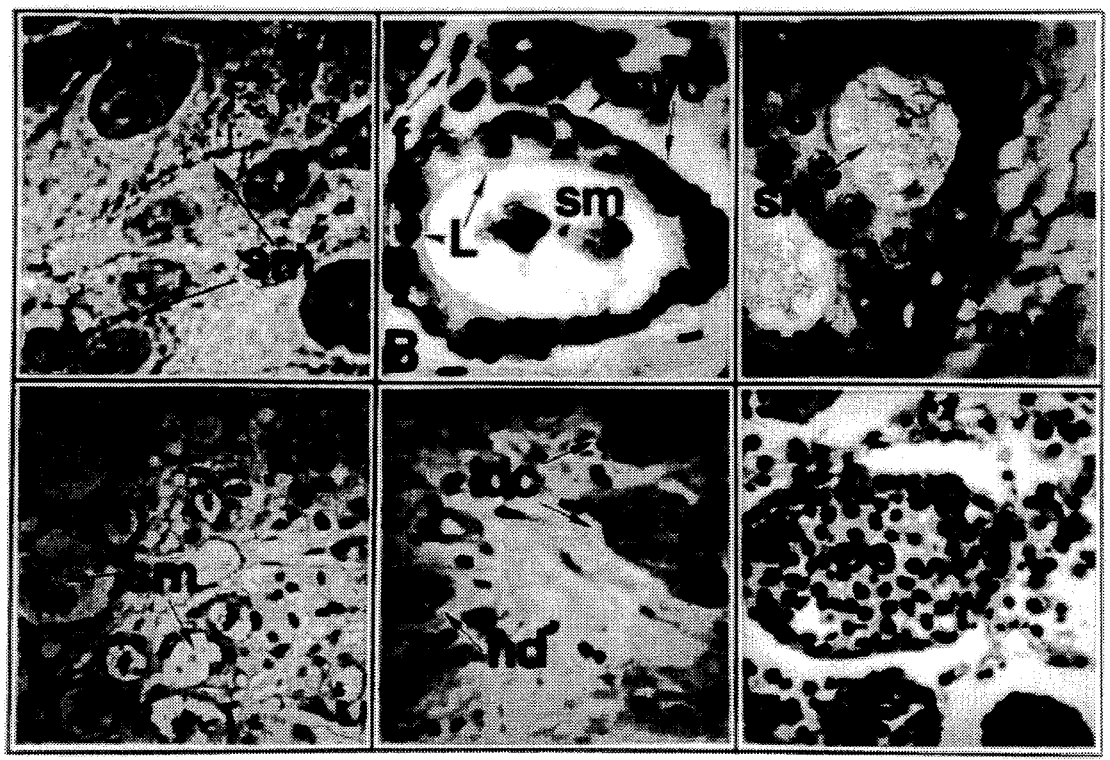
FIG. 6D   FIG. 6E   FIG. 6F
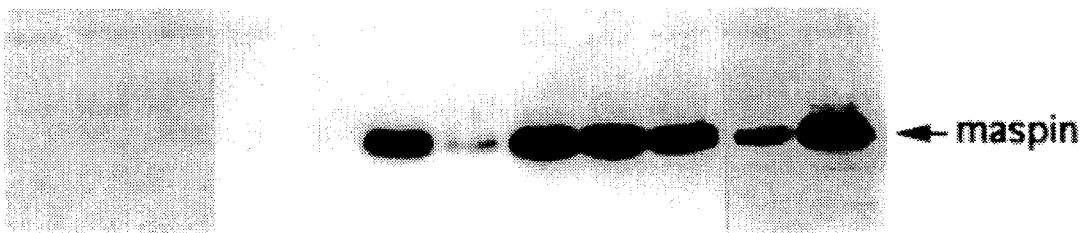
FIG. 7

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
  ( A ) LENGTH: 2584
  ( B ) TYPE: nucleic acid
  ( C ) STRANDEDNESS: double
  ( D ) TOPOLOGY: linear ( x i ) SEQUENCE DESCRIPTION: SEQ ID NO: 1:

```
GGCACGAGTT  GTGCTCCTCG  CTTGCCTGTT  CCTTTTCCAC  GCATTTCCA  GGATAACTGT           60

GACTCCAGGC  CCGCA ATG GAT GCC CTG CAA CTA GCA AAT TCG GCT TTT GCC              111
             Met Asp Ala Leu Gln Leu Ala Asn Ser Ala Phe Ala
              1               5                        10

GTT GAT CTG TTC AAA CAA CTA TGT GAA AAG GAG CCA CTG GGC AAT GTC                159
Val Asp Leu Phe Lys Gln Leu Cys Glu Lys Glu Pro Leu Gly Asn Val
         15                  20                  25

CTC TTC TCT CCA ATC TGT CTC TCC ACC TCT CTG TCA CTT GCT CAA GTG                207
Leu Phe Ser Pro Ile Cys Leu Ser Thr Ser Leu Ser Leu Ala Gln Val
         30                  35                  40

GGT GCT AAA GGT GAC ACT GCA AAT GAA ATT GGA CAG GTT CTT CAT TTT                255
Gly Ala Lys Gly Asp Thr Ala Asn Glu Ile Gly Gln Val Leu His Phe
45                   50                  55                  60

GAA AAT GTC AAA GAT ATA CCC TTT GGA TTT CAA ACA GTA ACA TCG GAT                303
Glu Asn Val Lys Asp Ile Pro Phe Gly Phe Gln Thr Val Thr Ser Asp
                 65                  70                  75

GTA AAC AAA CTT AGT TCC TTT TAC TCA CTG AAA CTA ATC AAG CGG CTC                351
Val Asn Lys Leu Ser Ser Phe Tyr Ser Leu Lys Leu Ile Lys Arg Leu
             80                  85                  90

TAC GTA GAC AAA TCT CTG AAT CTT TCT ACA GAG TTC ATC AGC TCT ACG                399
Tyr Val Asp Lys Ser Leu Asn Leu Ser Thr Glu Phe Ile Ser Ser Thr
         95                  100                 105

AAG AGA CCC TAT GCA AAG GAA TTG GAA ACT GTT GAC TTC AAA GAT AAA                447
Lys Arg Pro Tyr Ala Lys Glu Leu Glu Thr Val Asp Phe Lys Asp Lys
     110                 115                 120

TTG GAA GAA ACG AAA GGT CAG ATC AAC AAC TCA ATT AAG GAT CTC ACA                495
Leu Glu Glu Thr Lys Gly Gln Ile Asn Asn Ser Ile Lys Asp Leu Thr
125                 130                 135                 140

GAT GGC CAC TTT GAG AAC ATT TTA GCT GAC AAC AGT GTG AAC GAC CAG                543
Asp Gly His Phe Glu Asn Ile Leu Ala Asp Asn Ser Val Asn Asp Gln
                145                 150                 155

ACC AAA ATC CTT GTG GTT AAT GCT GCC TAC TTT GTT GGC AAG TGG ATG                591
Thr Lys Ile Leu Val Val Asn Ala Ala Tyr Phe Val Gly Lys Trp Met
            160                 165                 170

AAG AAA TTT CCT GAA TCA GAA ACA AAA GAA TGT CCT TTC AGA CTC AAC                639
Lys Lys Phe Pro Glu Ser Glu Thr Lys Glu Cys Pro Phe Arg Leu Asn
        175                 180                 185

AAG ACA GAC ACC AAA CCA GTG CAG ATG ATG AAC ATG GAG GCC ACG TTC                687
Lys Thr Asp Thr Lys Pro Val Gln Met Met Asn Met Glu Ala Thr Phe
    190                 195                 200

TGT ATG GGA AAC ATT GAC AGT ATC AAT TGT AAG ATC ATA GAG CTT CCT                735
Cys Met Gly Asn Ile Asp Ser Ile Asn Cys Lys Ile Ile Glu Leu Pro
205                 210                 215                 220

TTT CAA AAT AAG CAT CTC AGC ATG TTC ATC CTA CTA CCC AAG GAT GTG                783
Phe Gln Asn Lys His Leu Ser Met Phe Ile Leu Leu Pro Lys Asp Val
                225                 230                 235
```

```
GAG GAT GAG TCC ACA GGC TTG GAG AAG ATT GAA AAA CAA CTC AAC TCA        831
Glu Asp Glu Ser Thr Gly Leu Glu Lys Ile Glu Lys Gln Leu Asn Ser
            240                 245                 250

GAG TCA CTG TCA CAG TGG ACT AAT CCC AGC ACC ATG GCC AAT GCC AAG        879
Glu Ser Leu Ser Gln Trp Thr Asn Pro Ser Thr Met Ala Asn Ala Lys
        255                 260                 265

GTC AAA CTC TCC ATT CCA AAA TTT AAG GTG GAA AAG ATG ATT GAT CCC        927
Val Lys Leu Ser Ile Pro Lys Phe Lys Val Glu Lys Met Ile Asp Pro
        270                 275                 280

AAG GCT TGT CTG GAA AAT CTA GGG CTG AAA CAT ATC TTC AGT GAA GAC        975
Lys Ala Cys Leu Glu Asn Leu Gly Leu Lys His Ile Phe Ser Glu Asp
285                 290                 295                 300

ACA TCT GAT TTC TCT GGA ATG TCA GAG ACC AAG GGA GTG GCC CTA TCA       1023
Thr Ser Asp Phe Ser Gly Met Ser Glu Thr Lys Gly Val Ala Leu Ser
            305                 310                 315

AAT GTT ATC CAC AAA GTG TGC TTA GAA ATA ACT GAA GAT GGT GGG GAT       1071
Asn Val Ile His Lys Val Cys Leu Glu Ile Thr Glu Asp Gly Gly Asp
            320                 325                 330

TCC ATA GAG GTG CCA GGA GCA CGG ATC CTG CAG CAC AAG GAT GAA TTG       1119
Ser Ile Glu Val Pro Gly Ala Arg Ile Leu Gln His Lys Asp Glu Leu
        335                 340                 345

AAT GCT GAC CAT CCC TTT ATT TAC ATC ATC AGG CAC AAC AAA ACT CGA       1167
Asn Ala Asp His Pro Phe Ile Tyr Ile Ile Arg His Asn Lys Thr Arg
350                 355                 360

AAC ATC ATT TTC TTT GGC AAA TTC TGT TCT CCT  TAAGTGGCAT AGCCCATGTT    1220
Asn Ile Ile Phe Phe Gly Lys Phe Cys Ser Pro
365                 370                 375

AAGTCCTCCC TGACTTTCT GTGGATGCCG ATTTCTGTAA ACTCTGCATC CAGAGATTCA      1280

TTTTCTAGAT ACAATAAATT GCTAATGTTG CTGGATCAGG AAGCCGCCAG TACTTGTCAT     1340

ATGTAGCCTT CACACAGATA GACCTTTTTT TTTTTCCAAT TCTATCTTTT GTTTCCTTTT     1400

TTCCCATAAG ACAATGACAT ACGCTTTTAA TGAAAAGGAA TCACGTTAGA GGAAAAATAT     1460

TTATTCATTA TTTGTCAAAT TGTCCGGGGT AGTTGGCAGA AATACAGTCT TCCACAAAGA     1520

AAATTCCTAT AAGGAAGATT TGGAAGCTCT TCTTCCCAGC ACTATGCTTT CCTTCTTTGG     1580

GATAGAGAAT GTTCCAGACA TTCTCGCTTC CCTGAAAGAC TGAAGAAAGT GTAGTGCATG     1640

GGACCCACGA AACTGCCCTG GCTCCAGTGA AACTTGGGCA CATGCTCAGG CTACTATAGG     1700

TCCAGAAGTC CTTATGTTAA GCCCTGGCAG GCAGGTGTTT ATTAAAATTC TGAATTTTGG     1760

GGATTTTCAA AAGATAATAT TTTACATACA CTGTATGTTA TAGAACTTCA TGGATCAGAT     1820

CTGGGGCAGC AACCTATAAA TCAACACCTT AATATGCTGC AACAAATGT AGAATATTCA      1880

GACAAAATGG ATACATAAAG ACTAAGTAGC CCATAAGGGG TCAAAATTTG CTGCCAAATG     1940

CGTATGCCAC CAACTTACAA AAACACTTCG TTCGCAGAGC TTTTCAGATT GTGGAATGTT    2000

GGATAAGGAA TTATAGACCT CTAGTAGCTG AAATGCAAGA CCCCAAGAGG AAGTTCAGAT     2060

CTTAATATAA ATTCACTTTC ATTTTTGATA GCTGTCCCAT CTGGTCATGT GGTTGGCACT     2120

AGACTGGTGG CAGGGCTTC TAGCTGACTC GCACAGGGAT TCTCACAATA GCCGATATCA      2180

GAATTTGTGT TGAAGGAACT TGTCTCTTCA TCTAATATGA TAGCGGGAAA AGGAGAGGAA     2240

ACTACTGCCT TTAGAAAATA TAAGTAAAGT GATTAAAGTG CTCACGTTAC CTTGACACAT     2300

AGTTTTTCAG TCTATGGGTT TAGTTACTTT AGATGGCAAG CATGTAACTT ATATTAATAG     2360

TAATTTGTAA AGTTGGGTGG ATAAGCTATC CCTGTTGCCG GTTCATGGAT TACTTCTCTA     2420

TAAAAAATAT ATATTTACCA AAAAATTTTG TGACATTCCT TCTCCCATCT CTTCCTTGAC     2480
```

```
ATGCATTGTA AATAGGTTCT TCTTGTTCTG AGATTCAATA TTGAATTTCT CCTATGCTAT      2540

TGACAATAAA ATATTATTGA ACTACCAAAA AAAAAAAAAA AAAA                       2584
```

( 2 ) INFORMATION FOR SEQ ID NO: 2:

( i ) SEQUENCE CHARACTERISTICS:
        ( A ) LENGTH: 375
        ( B ) TYPE: amino acid
        ( C ) STRANDEDNESS:
        ( D ) TOPOLOGY: linear ( x i ) SEQUENCE DESCRIPTION: SEQ ID NO: 2:

```
Met Asp Ala Leu Gln Leu Ala Asn Ser Ala Phe Ala Val Asp Leu Phe
 1               5                  10                  15

Lys Gln Leu Cys Glu Lys Glu Pro Leu Gly Asn Val Leu Phe Ser Pro
             20                  25                  30

Ile Cys Leu Ser Thr Ser Leu Ser Leu Ala Gln Val Gly Ala Lys Gly
         35                  40                  45

Asp Thr Ala Asn Glu Ile Gly Gln Val Leu His Phe Glu Asn Val Lys
     50                  55                  60

Asp Ile Pro Phe Gly Phe Gln Thr Val Thr Ser Asp Val Asn Lys Leu
 65                  70                  75                  80

Ser Ser Phe Tyr Ser Leu Lys Leu Ile Lys Arg Leu Tyr Val Asp Lys
                 85                  90                  95

Ser Leu Asn Leu Ser Thr Glu Phe Ile Ser Ser Thr Lys Arg Pro Tyr
                100                 105                 110

Ala Lys Glu Leu Glu Thr Val Asp Phe Lys Asp Lys Leu Glu Glu Thr
            115                 120                 125

Lys Gly Gln Ile Asn Asn Ser Ile Lys Asp Leu Thr Asp Gly His Phe
        130                 135                 140

Glu Asn Ile Leu Ala Asp Asn Ser Val Asn Asp Gln Thr Lys Ile Leu
145                 150                 155                 160

Val Val Asn Ala Ala Tyr Phe Val Gly Lys Trp Met Lys Lys Phe Pro
                165                 170                 175

Glu Ser Glu Thr Lys Glu Cys Pro Phe Arg Leu Asn Lys Thr Asp Thr
            180                 185                 190

Lys Pro Val Gln Met Met Asn Met Glu Ala Thr Phe Cys Met Gly Asn
        195                 200                 205

Ile Asp Ser Ile Asn Cys Lys Ile Ile Glu Leu Pro Phe Gln Asn Lys
    210                 215                 220

His Leu Ser Met Phe Ile Leu Leu Pro Lys Asp Val Glu Asp Glu Ser
225                 230                 235                 240

Thr Gly Leu Glu Lys Ile Glu Lys Gln Leu Asn Ser Glu Ser Leu Ser
                245                 250                 255

Gln Trp Thr Asn Pro Ser Thr Met Ala Asn Ala Lys Val Lys Leu Ser
            260                 265                 270

Ile Pro Lys Phe Lys Val Glu Lys Met Ile Asp Pro Lys Ala Cys Leu
        275                 280                 285

Glu Asn Leu Gly Leu Lys His Ile Phe Ser Glu Asp Thr Ser Asp Phe
    290                 295                 300

Ser Gly Met Ser Glu Thr Lys Gly Val Ala Leu Ser Asn Val Ile His
305                 310                 315                 320

Lys Val Cys Leu Glu Ile Thr Glu Asp Gly Gly Asp Ser Ile Glu Val
                325                 330                 335

Pro Gly Ala Arg Ile Leu Gln His Lys Asp Glu Leu Asn Ala Asp His
```

|   | 340 |   |   |   | 345 |   |   |   | 350 |   |   |   |
|---|---|---|---|---|---|---|---|---|---|---|---|---|

Pro Phe Ile Tyr Ile Ile Arg His Asn Lys Thr Arg Asn Ile Ile Phe
            355                   360                  365

Phe Gly Lys Phe Cys Ser Pro
370                 375

( 2 ) INFORMATION FOR SEQ ID NO: 3:

( i ) SEQUENCE CHARACTERISTICS:
        ( A ) LENGTH: 418
        ( B ) TYPE: amino acid
        ( C ) STRANDEDNESS:
        ( D ) TOPOLOGY: linear ( x i ) SEQUENCE DESCRIPTION: SEQ ID NO: 3:

Met Pro Ser Ser Val Ser Trp Gly Ile Leu Leu Leu Ala Gly Leu Cys
1                     5                   10                 15

Cys Leu Val Pro Val Ser Leu Ala Glu Asp Pro Gln Gly Asp Ala Ala
             20                   25                  30

Gln Lys Thr Asp Thr Ser His His Asp Gln Asp His Pro Thr Phe Asn
        35                   40                  45

Lys Ile Thr Pro Asn Leu Ala Glu Phe Ala Phe Ser Leu Tyr Arg Gln
50                    55                  60

Leu Ala His Gln Ser Asn Ser Thr Asn Ile Phe Phe Ser Pro Val Ser
65                  70                  75              80

Ile Ala Thr Ala Phe Ala Met Leu Ser Leu Gly Thr Lys Ala Asp Thr
             85                   90                  95

His Asp Glu Ile Leu Glu Gly Leu Asn Phe Asn Leu Thr Glu Ile Pro
             100                 105              110

Glu Ala Gln Ile His Glu Gly Phe Gln Glu Leu Leu Arg Thr Leu Asn
        115                 120              125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155            160

Leu Tyr His Ser Glu Ala Phe Thr Val Asn Phe Gly Asp Thr Glu Glu
             165                 170              175

Ala Lys Lys Gln Ile Asn Asp Tyr Val Glu Lys Gly Thr Gln Gly Lys
        180                 185              190

Ile Val Asp Leu Val Lys Glu Leu Asp Arg Asp Thr Val Phe Ala Leu
    195                 200              205

Val Asn Tyr Ile Phe Phe Lys Gly Lys Trp Glu Arg Pro Phe Glu Val
210                 215                 220

Lys Asp Thr Glu Glu Glu Asp Phe His Val Asp Gln Val Thr Thr Val
225                 230                 235            240

Lys Val Pro Met Met Lys Arg Leu Gly Met Phe Asn Ile Gln His Cys
             245                 250              255

Lys Lys Leu Ser Ser Trp Val Leu Leu Met Lys Tyr Leu Gly Asn Ala
        260                 265              270

Thr Ala Ile Phe Phe Leu Pro Asp Glu Gly Lys Leu Gln His Leu Glu
    275                 280                 285

Asn Glu Leu Thr His Asp Ile Ile Thr Lys Phe Leu Glu Asn Glu Asp
    290                 295                 300

Arg Arg Ser Ala Ser Leu His Leu Pro Lys Leu Ser Ile Thr Gly Thr
305                 310                 315            320

| Tyr | Asp | Leu | Lys | Ser | Val | Leu | Gly | Gln | Leu | Gly | Ile | Thr | Lys | Val | Phe |
|-----|-----|-----|-----|-----|-----|-----|-----|-----|-----|-----|-----|-----|-----|-----|-----|
|     |     |     |     | 325 |     |     |     |     | 330 |     |     |     |     | 335 |     |

| Ser | Asn | Gly | Ala | Asp | Leu | Ser | Gly | Val | Thr | Glu | Glu | Ala | Pro | Leu | Lys |
|-----|-----|-----|-----|-----|-----|-----|-----|-----|-----|-----|-----|-----|-----|-----|-----|
|     |     |     | 340 |     |     |     |     | 345 |     |     |     |     | 350 |     |     |

| Leu | Ser | Lys | Ala | Val | His | Lys | Ala | Val | Leu | Thr | Ile | Asp | Glu | Lys | Gly |
|-----|-----|-----|-----|-----|-----|-----|-----|-----|-----|-----|-----|-----|-----|-----|-----|
|     |     | 355 |     |     |     |     | 360 |     |     |     |     | 365 |     |     |     |

| Thr | Glu | Ala | Ala | Gly | Ala | Met | Phe | Leu | Glu | Ala | Ile | Pro | Met | Ser | Ile |
|-----|-----|-----|-----|-----|-----|-----|-----|-----|-----|-----|-----|-----|-----|-----|-----|
|     | 370 |     |     |     |     |     | 375 |     |     |     |     | 380 |     |     |     |

| Pro | Pro | Glu | Val | Lys | Phe | Asn | Lys | Pro | Phe | Val | Phe | Leu | Met | Ile | Glu |
|-----|-----|-----|-----|-----|-----|-----|-----|-----|-----|-----|-----|-----|-----|-----|-----|
| 385 |     |     |     |     |     | 390 |     |     |     |     | 395 |     |     |     | 400 |

| Gln | Asn | Thr | Lys | Ser | Pro | Leu | Phe | Met | Gly | Lys | Val | Val | Asn | Pro | Thr |
|-----|-----|-----|-----|-----|-----|-----|-----|-----|-----|-----|-----|-----|-----|-----|-----|
|     |     |     |     | 405 |     |     |     |     | 410 |     |     |     |     | 415 |     |

| Gln | Lys |
|-----|-----|

(2) INFORMATION FOR SEQ ID NO: 4:

(i) SEQUENCE CHARACTERISTICS:
        (A) LENGTH: 379
        (B) TYPE: amino acid
        (C) STRANDEDNESS:
        (D) TOPOLOGY: linear (xi) SEQUENCE DESCRIPTION: SEQ ID NO: 4:

| Met | Glu | Gln | Leu | Ser | Ser | Ala | Asn | Thr | Arg | Phe | Ala | Leu | Asp | Leu | Phe |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Leu | Ala | Leu | Ser | Glu | Asn | Asn | Pro | Ala | Gly | Asn | Ile | Phe | Ile | Ser | Pro |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Phe | Ser | Ile | Ser | Ser | Ala | Met | Ala | Met | Val | Phe | Leu | Gly | Thr | Arg | Gly |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Asn | Thr | Ala | Ala | Gln | Leu | Ser | Lys | Thr | Phe | His | Phe | Asn | Thr | Val | Glu |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Glu | Val | His | Ser | Arg | Phe | Gln | Ser | Leu | Asn | Ala | Asp | Ile | Asn | Lys | Arg |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Gly | Ala | Ser | Tyr | Ile | Leu | Lys | Leu | Ala | Asn | Arg | Leu | Tyr | Gly | Glu | Lys |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Thr | Tyr | Asn | Phe | Leu | Pro | Glu | Phe | Leu | Val | Ser | Thr | Gln | Lys | Thr | Tyr |
|-----|-----|-----|-----|-----|-----|-----|-----|-----|-----|-----|-----|-----|-----|-----|-----|
|     |     |     |     | 100 |     |     |     |     | 105 |     |     |     |     | 110 |     |

| Gly | Ala | Asp | Leu | Ala | Ser | Val | Asp | Phe | Gln | His | Ala | Ser | Glu | Asp | Ala |
|-----|-----|-----|-----|-----|-----|-----|-----|-----|-----|-----|-----|-----|-----|-----|-----|
|     |     |     | 115 |     |     |     |     | 120 |     |     |     |     | 125 |     |     |

| Arg | Lys | Thr | Ile | Asn | Gln | Trp | Val | Lys | Gly | Gln | Thr | Glu | Gly | Lys | Ile |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Pro | Glu | Leu | Leu | Ala | Ser | Gly | Met | Val | Asp | Asn | Met | Thr | Lys | Leu | Val |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Leu | Val | Asn | Ala | Ile | Tyr | Phe | Lys | Gly | Asn | Trp | Lys | Asp | Lys | Phe | Met |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Lys | Glu | Ala | Thr | Thr | Asn | Ala | Pro | Phe | Arg | Leu | Asn | Lys | Lys | Asp | Arg |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Lys | Thr | Val | Lys | Met | Met | Tyr | Gln | Lys | Lys | Lys | Phe | Ala | Tyr | Gly | Tyr |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Ile | Glu | Asp | Leu | Lys | Cys | Arg | Val | Leu | Glu | Leu | Pro | Tyr | Gln | Gly | Glu |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Glu | Leu | Ser | Met | Val | Ile | Leu | Leu | Pro | Asp | Asp | Ile | Glu | Asp | Glu | Ser |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Thr | Gly | Leu | Lys | Lys | Ile | Glu | Glu | Gln | Leu | Thr | Leu | Glu | Lys | Leu | His |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Glu | Trp | Thr | Lys<br>260 | Pro | Glu | Asn | Leu | Asp<br>265 | Phe | Ile | Glu | Val | Asn<br>270 | Val | Ser |

| Leu | Pro | Arg<br>275 | Phe | Lys | Leu | Glu | Glu<br>280 | Ser | Tyr | Thr | Leu | Asn<br>285 | Ser | Asp | Leu |

| Ala | Arg<br>290 | Leu | Gly | Val | Gln | Asp<br>295 | Leu | Phe | Asn | Ser | Ser<br>300 | Lys | Ala | Asp | Leu |

| Ser<br>305 | Gly | Met | Ser | Gly | Ala<br>310 | Arg | Asp | Ile | Phe | Ile<br>315 | Ser | Lys | Ile | Val | His<br>320 |

| Lys | Ser | Phe | Val | Glu<br>325 | Val | Asn | Glu | Glu | Gly<br>330 | Thr | Glu | Ala | Ala | Ala<br>335 | Ala |

| Thr | Ala | Gly | Ile<br>340 | Ala | Thr | Phe | Cys | Met<br>345 | Leu | Met | Pro | Glu | Glu<br>350 | Asn | Phe |

| Thr | Ala | Asp<br>355 | His | Pro | Phe | Leu | Phe<br>360 | Phe | Ile | Arg | His | Asn<br>365 | Ser | Ser | Gly |

| Ser | Ile | Leu<br>370 | Phe | Leu | Gly | Arg<br>375 | Phe | Ser | Ser | Pro | | | | | |

( 2 ) INFORMATION FOR SEQ ID NO: 5:

( i ) SEQUENCE CHARACTERISTICS:
        ( A ) LENGTH: 375
        ( B ) TYPE: amino acid
        ( C ) STRANDEDNESS:
        ( D ) TOPOLOGY: linear ( x i ) SEQUENCE DESCRIPTION: SEQ ID NO: 5:

| Gly<br>1 | Ser | Ile | Gly | Ala<br>5 | Ala | Ser | Met | Glu | Phe<br>10 | Cys | Phe | Asp | Val | Phe<br>15 | Lys |

| Glu | Leu | Lys | Val<br>20 | His | His | Ala | Asn | Glu<br>25 | Asn | Ile | Phe | Tyr | Cys<br>30 | Pro | Ile |

| Ala | Ile | Met<br>35 | Ser | Ala | Leu | Ala | Met<br>40 | Val | Tyr | Leu | Gly | Ala<br>45 | Lys | Asp | Ser |

| Thr | Arg<br>50 | Thr | Gln | Ile | Asn | Lys<br>55 | Val | Val | Arg | Phe | Asp<br>60 | Lys | Leu | Pro | Gly |

| Phe<br>65 | Gly | Asp | Ser | Ile | Glu<br>70 | Ala | Gln | Cys | Gly | Thr<br>75 | Ser | Val | Asn | Val | His<br>80 |

| Ser | Ser | Leu | Arg | Asp<br>85 | Ile | Leu | Asn | Gln | Ile<br>90 | Thr | Lys | Pro | Asn | Asp<br>95 | Val |

| Tyr | Ser | Phe | Ser<br>100 | Leu | Ala | Ser | Arg | Leu<br>105 | Tyr | Ala | Glu | Glu | Arg<br>110 | Tyr | Pro |

| Ile | Leu | Pro<br>115 | Glu | Tyr | Leu | Gln | Cys<br>120 | Val | Lys | Glu | Leu | Tyr<br>125 | Arg | Gly | Gly |

| Leu | Glu<br>130 | Pro | Ile | Asn | Phe | Gln<br>135 | Thr | Ala | Ala | Asp | Gln<br>140 | Ala | Arg | Glu | Leu |

| Ile<br>145 | Asn | Ser | Trp | Val | Glu<br>150 | Ser | Gln | Thr | Asn | Gly<br>155 | Ile | Ile | Arg | Asn | Val<br>160 |

| Leu | Gln | Pro | Ser | Ser<br>165 | Val | Asp | Ser | Gln | Thr<br>170 | Ala | Met | Val | Leu | Val<br>175 | Asn |

| Ala | Ile | Val | Phe<br>180 | Lys | Gly | Leu | Trp | Glu<br>185 | Lys | Ala | Phe | Lys | Asp<br>190 | Glu | Asp |

| Thr | Gln<br>195 | Ala | Met | Pro | Phe | Arg<br>200 | Val | Thr | Glu | Gln | Glu<br>205 | Ser | Lys | Pro | Val |

| Gln | Met<br>210 | Met | Tyr | Gln | Ile | Gly<br>215 | Leu | Phe | Arg | Val | Ala<br>220 | Ser | Met | Ala | Ser |

| Glu<br>225 | Lys | Met | Lys | Ile | Leu<br>230 | Glu | Leu | Pro | Phe | Ala<br>235 | Ser | Gly | Thr | Met | Ser<br>240 |

-continued

| Met | Leu | Val | Leu | Leu | Pro | Asp | Glu | Val | Ser | Gly | Leu | Glu | Gln | Leu | Glu |
|---|---|---|---|---|---|---|---|---|---|---|---|---|---|---|---|
| | | | | 245 | | | | | 250 | | | | | 255 | |

| Ser | Ile | Ile | Asn | Phe | Glu | Lys | Leu | Thr | Glu | Trp | Thr | Ser | Ser | Asn | Val |
|---|---|---|---|---|---|---|---|---|---|---|---|---|---|---|---|
| | | | 260 | | | | | 265 | | | | | 270 | | |

| Met | Glu | Glu | Arg | Lys | Ile | Lys | Val | Tyr | Leu | Pro | Arg | Met | Lys | Met | Glu |
|---|---|---|---|---|---|---|---|---|---|---|---|---|---|---|---|
| | | 275 | | | | | 280 | | | | | 285 | | | |

| Glu | Lys | Tyr | Asn | Leu | Thr | Ser | Val | Leu | Met | Ala | Met | Gly | Ile | Thr | Asp |
|---|---|---|---|---|---|---|---|---|---|---|---|---|---|---|---|
| | 290 | | | | | 295 | | | | | 300 | | | | |

| Val | Phe | Ser | Ser | Ser | Ala | Asn | Leu | Ser | Gly | Ile | Ser | Ser | Ala | Glu | Ser |
|---|---|---|---|---|---|---|---|---|---|---|---|---|---|---|---|
| 305 | | | | | 310 | | | | | 315 | | | | | 320 |

| Leu | Lys | Ile | Ser | Gln | Ala | Val | His | Ala | Ala | His | Ala | Glu | Ile | Asn | Glu |
|---|---|---|---|---|---|---|---|---|---|---|---|---|---|---|---|
| | | | | 325 | | | | | 330 | | | | | 335 | |

| Ala | Gly | Arg | Glu | Val | Val | Gly | Ser | Ala | Glu | Ala | Gly | Val | Asp | Ala | Ala |
|---|---|---|---|---|---|---|---|---|---|---|---|---|---|---|---|
| | | | 340 | | | | | 345 | | | | | 350 | | |

| Ser | Val | Ser | Glu | Glu | Phe | Arg | Ala | Asp | His | Pro | Phe | Leu | Phe | Cys | Ile |
|---|---|---|---|---|---|---|---|---|---|---|---|---|---|---|---|
| | | 355 | | | | | 360 | | | | | 365 | | | |

| Lys | His | Ile | Ala | Thr | Asn | Ala |
|---|---|---|---|---|---|---|
| | 370 | | | | | 375 |

(2) INFORMATION FOR SEQ ID NO: 6:

(i) SEQUENCE CHARACTERISTICS:
(A) LENGTH: 390
(B) TYPE: amino acid
(C) STRANDEDNESS:
(D) TOPOLOGY: linear (xi) SEQUENCE DESCRIPTION: SEQ ID NO: 6:

| Met | Gln | Met | Ser | Pro | Ala | Leu | Thr | Cys | Leu | Val | Leu | Gly | Leu | Ala | Ile |
|---|---|---|---|---|---|---|---|---|---|---|---|---|---|---|---|
| 1 | | | | 5 | | | | | 10 | | | | | 15 | |

| Val | Phe | Gly | Glu | Gly | Ser | Ala | Val | His | His | Pro | Pro | Ser | Tyr | Val | Ala |
|---|---|---|---|---|---|---|---|---|---|---|---|---|---|---|---|
| | | | 20 | | | | | 25 | | | | | 30 | | |

| His | Leu | Ala | Ser | Asp | Phe | Gly | Val | Arg | Val | Phe | Gln | Gln | Val | Ala | Gln |
|---|---|---|---|---|---|---|---|---|---|---|---|---|---|---|---|
| | | 35 | | | | | 40 | | | | | 45 | | | |

| Ala | Ser | Lys | Asp | Arg | Asn | Val | Val | Phe | Ser | Pro | Tyr | Gly | Val | Ala | Ser |
|---|---|---|---|---|---|---|---|---|---|---|---|---|---|---|---|
| | 50 | | | | | 55 | | | | | 60 | | | | |

| Val | Leu | Ala | Met | Leu | Gln | Leu | Thr | Thr | Gly | Gly | Glu | Thr | Gln | Gln | Gln |
|---|---|---|---|---|---|---|---|---|---|---|---|---|---|---|---|
| 65 | | | | | 70 | | | | | 75 | | | | | 80 |

| Ile | Gln | Ala | Ala | Met | Gly | Phe | Lys | Ile | Asp | Asp | Lys | Gly | Met | Ala | Pro |
|---|---|---|---|---|---|---|---|---|---|---|---|---|---|---|---|
| | | | | 85 | | | | | 90 | | | | | 95 | |

| Ala | Leu | Arg | His | Leu | Tyr | Lys | Glu | Leu | Met | Gly | Pro | Trp | Asn | Lys | Asp |
|---|---|---|---|---|---|---|---|---|---|---|---|---|---|---|---|
| | | | 100 | | | | | 105 | | | | | 110 | | |

| Glu | Ile | Ser | Thr | Thr | Asp | Ala | Ile | Phe | Val | Gln | Arg | Asp | Leu | Lys | Leu |
|---|---|---|---|---|---|---|---|---|---|---|---|---|---|---|---|
| | | 115 | | | | | 120 | | | | | 125 | | | |

| Val | Gln | Gly | Phe | Met | Pro | His | Phe | Phe | Arg | Leu | Phe | Arg | Ser | Thr | Val |
|---|---|---|---|---|---|---|---|---|---|---|---|---|---|---|---|
| | 130 | | | | | 135 | | | | | 140 | | | | |

| Lys | Gln | Val | Asp | Phe | Ser | Glu | Val | Glu | Arg | Ala | Arg | Phe | Ile | Ile | Asn |
|---|---|---|---|---|---|---|---|---|---|---|---|---|---|---|---|
| 145 | | | | | 150 | | | | | 155 | | | | | 160 |

| Asp | Trp | Val | Lys | Thr | His | Thr | Lys | Gly | Met | Ile | Ser | Asn | Leu | Leu | Gly |
|---|---|---|---|---|---|---|---|---|---|---|---|---|---|---|---|
| | | | | 165 | | | | | 170 | | | | | 175 | |

| Lys | Gly | Ala | Val | Asp | Gln | Leu | Thr | Arg | Leu | Val | Leu | Val | Asn | Ala | Leu |
|---|---|---|---|---|---|---|---|---|---|---|---|---|---|---|---|
| | | | 180 | | | | | 185 | | | | | 190 | | |

| Tyr | Phe | Asn | Gly | Gln | Trp | Lys | Thr | Pro | Phe | Pro | Asp | Ser | Ser | Thr | His |
|---|---|---|---|---|---|---|---|---|---|---|---|---|---|---|---|
| | | 195 | | | | | 200 | | | | | 205 | | | |

| Arg | Arg | Leu | Phe | His | Lys | Ser | Asp | Gly | Ser | Thr | Val | Ser | Val | Pro | Met |

|   | 210 |   |   |   |   | 215 |   |   |   |   | 220 |   |   |   |
|---|---|---|---|---|---|---|---|---|---|---|---|---|---|---|
| Met 225 | Ala | Gln | Thr | Asn | Lys 230 | Phe | Asn | Tyr | Thr | Glu 235 | Phe | Thr | Thr | Pro | Asp 240 |
| Gly | His | Tyr | Tyr | Asp 245 | Ile | Leu | Glu | Leu | Pro 250 | Tyr | His | Gly | Asp | Thr 255 | Leu |
| Ser | Met | Phe | Ile 260 | Ala | Ala | Pro | Tyr | Glu 265 | Lys | Glu | Val | Pro | Leu 270 | Ser | Ala |
| Leu | Thr | Asn 275 | Ile | Leu | Ser | Ala | Gln 280 | Leu | Ile | Ser | His | Trp 285 | Lys | Gly | Asn |
| Met | Thr 290 | Arg | Leu | Pro | Arg 295 | Leu | Val | Leu | Pro | Lys 300 | Phe | Ser | Leu | Glu |
| Thr 305 | Glu | Val | Asp | Leu | Arg 310 | Lys | Pro | Leu | Glu | Asn 315 | Leu | Gly | Met | Thr | Asp 320 |
| Met | Phe | Arg | Gln | Phe 325 | Gln | Ala | Asp | Phe | Thr 330 | Ser | Leu | Ser | Asp | Gln 335 | Glu |
| Pro | Leu | His | Val 340 | Ala | Gln | Ala | Leu | Gln 345 | Lys | Val | Lys | Ile | Glu 350 | Val | Asn |
| Glu | Ser | Gly 355 | Thr | Val | Ala | Ser | Ser 360 | Ser | Thr | Ala | Val | Ile 365 | Val | Ser | Ala |
| Arg | Met 370 | Ala | Pro | Glu | Glu | Ile 375 | Ile | Met | Asp | Arg | Pro 380 | Phe | Leu | Phe | Val |
| Val 385 | Arg | His | Asn | Pro | Thr 390 |   |   |   |   |   |   |   |   |   |   |

( 2 ) INFORMATION FOR SEQ ID NO: 7:

( i ) SEQUENCE CHARACTERISTICS:
        ( A ) LENGTH: 405
        ( B ) TYPE: amino acid
        ( C ) STRANDEDNESS:
        ( D ) TOPOLOGY: linear ( x i ) SEQUENCE DESCRIPTION: SEQ ID NO: 7:

| Met 1 | Glu | Asp | Leu | Cys 5 | Val | Ala | Asn | Thr | Leu 10 | Phe | Ala | Leu | Asn | Leu 15 | Phe |
|---|---|---|---|---|---|---|---|---|---|---|---|---|---|---|---|
| Lys | His | Leu | Ala 20 | Lys | Ala | Ser | Pro | Thr 25 | Gln | Asn | Leu | Phe | Leu 30 | Ser | Pro |
| Trp | Ser | Ile 35 | Ser | Ser | Thr | Met | Ala 40 | Met | Val | Tyr | Met | Gly 45 | Ser | Arg | Gly |
| Ser | Thr | Glu 50 | Asp | Gln | Met | Ala | Lys 55 | Val | Leu | Gln | Phe | Asn 60 | Glu | Val | Gly |
| Ala 65 | Asn | Ala | Val | Thr | Pro 70 | Met | Thr | Pro | Glu | Asn 75 | Phe | Thr | Ser | Cys | Gly 80 |
| Phe | Met | Gln | Gln | Ile 85 | Gln | Lys | Gly | Ser | Tyr 90 | Pro | Asp | Ala | Ile | Leu 95 | Gln |
| Ala | Gln | Ala | Ala 100 | Asp | Lys | Ile | His | Ser 105 | Ser | Phe | Arg | Ser | Leu 110 | Ser | Ser |
| Ala | Ile | Asn 115 | Ala | Ser | Thr | Gly | Asp 120 | Tyr | Leu | Leu | Glu | Ser 125 | Val | Asn | Lys |
| Leu | Phe 130 | Gly | Glu | Lys | Ser | Ala 135 | Ser | Phe | Arg | Glu | Glu 140 | Tyr | Ile | Arg | Leu |
| Cys 145 | Gln | Lys | Tyr | Tyr | Ser 150 | Ser | Glu | Pro | Gln | Ala 155 | Val | Asp | Phe | Leu | Glu 160 |
| Cys | Ala | Glu | Glu | Ala 165 | Arg | Lys | Lys | Ile | Asn 170 | Ser | Trp | Val | Lys | Thr 175 | Gln |

```
Thr Lys Gly Lys Ile Pro Asn Leu Leu Pro Glu Gly Ser Val Asp Gly
        180                 185                 190

Asp Thr Arg Met Val Leu Val Asn Ala Val Tyr Phe Lys Gly Lys Trp
        195                 200                 205

Lys Thr Pro Phe Glu Lys Lys Leu Asn Gly Leu Tyr Pro Phe Arg Val
        210                 215                 220

Asn Ser Ala Gln Arg Thr Pro Val Gln Met Met Tyr Leu Arg Glu Lys
225                 230                 235                 240

Leu Asn Ile Gly Tyr Ile Glu Asp Leu Lys Ala Gln Ile Leu Glu Leu
                245                 250                 255

Pro Tyr Ala Gly Asp Val Ser Met Phe Leu Leu Leu Pro Asp Glu Ile
                260                 265                 270

Ala Asp Val Ser Thr Gly Leu Glu Leu Leu Glu Ser Glu Ile Thr Tyr
        275                 280                 285

Asp Lys Leu Asn Lys Trp Thr Ser Lys Asp Lys Met Ala Glu Asp Glu
        290                 295                 300

Val Glu Val Tyr Ile Pro Gln Phe Lys Leu Glu Glu His Tyr Glu Leu
305                 310                 315                 320

Arg Ser Ile Leu Arg Ser Met Gly Met Glu Asp Ala Phe Asn Lys Gly
                325                 330                 335

Arg Ala Asn Phe Ser Gly Met Ser Glu Arg Asn Asp Leu Phe Leu Ser
                340                 345                 350

Glu Val Phe His Gln Ala Met Val Asp Val Asn Glu Glu Gly Thr Glu
        355                 360                 365

Ala Ala Ala Gly Thr Gly Gly Val Met Thr Gly Arg Thr Gly His Gly
        370                 375                 380

Gly Pro Gln Phe Val Ala Asp His Pro Phe Leu Phe Leu Ile Met His
385                 390                 395                 400

Lys Ile Thr Lys Cys
                405

( 2 ) INFORMATION FOR SEQ ID NO: 8:

( i ) SEQUENCE CHARACTERISTICS:
                ( A ) LENGTH: 375
                ( B ) TYPE: amino acid
                ( C ) STRANDEDNESS:
                ( D ) TOPOLOGY: linear ( x i ) SEQUENCE DESCRIPTION: SEQ ID NO: 8:

Met Glu Gln Leu Ser Thr Ala Asn Thr His Phe Ala Val Asp Leu Phe
1               5                   10                  15

Arg Ala Leu Asn Glu Ser Asp Pro Thr Gly Asn Ile Phe Ile Ser Pro
                20                  25                  30

Leu Ser Ile Ser Ser Ala Leu Ala Met Ile Phe Leu Gly Thr Arg Gly
            35                  40                  45

Asn Thr Ala Ala Gln Val Ser Lys Ala Leu Tyr Phe Asp Thr Val Glu
        50                  55                  60

Asp Ile His Ser Arg Phe Gln Ser Leu Asn Ala Asp Ile Asn Lys Pro
65                  70                  75                  80

Gly Ala Pro Tyr Ile Leu Lys Leu Ala Asn Arg Leu Tyr Gly Glu Lys
                85                  90                  95

Thr Tyr Asn Phe Leu Ala Asp Phe Leu Ala Ser Thr Gln Lys Met Tyr
                100                 105                 110

Gly Ala Glu Leu Ala Ser Val Asp Phe Gln Gln Ala Pro Glu Asp Ala
            115                 120                 125
```

| | | | | | | | | | | | | | | |
|---|---|---|---|---|---|---|---|---|---|---|---|---|---|---|
| Arg | Lys 130 | Glu | Ile | Asn | Glu | Trp 135 | Val | Lys | Gly | Gln | Thr 140 | Glu | Gly | Lys | Ile |
| Pro 145 | Glu | Leu | Leu | Val | Lys 150 | Gly | Met | Val | Asp | Asn 155 | Met | Thr | Lys | Leu | Val 160 |
| Leu | Val | Asn | Ala | Ile 165 | Tyr | Phe | Lys | Gly | Asn 170 | Trp | Gln | Glu | Lys | Phe 175 | Met |
| Lys | Glu | Ala | Thr 180 | Arg | Asp | Ala | Pro | Phe 185 | Arg | Leu | Asn | Lys | Lys 190 | Asp | Thr |
| Lys | Thr | Val 195 | Lys | Met | Met | Tyr | Gln 200 | Lys | Lys | Lys | Phe | Pro 205 | Tyr | Asn | Tyr |
| Ile | Glu 210 | Asp | Leu | Lys | Cys | Arg 215 | Val | Leu | Glu | Leu | Pro 220 | Tyr | Gln | Gly | Lys |
| Glu 225 | Leu | Ser | Met | Ile | Ile 230 | Leu | Leu | Pro | Asp | Asp 235 | Ile | Glu | Asp | Glu | Ser 240 |
| Thr | Gly | Leu | Glu | Lys 245 | Ile | Glu | Lys | Gln | Leu 250 | Thr | Leu | Glu | Lys | Leu 255 | Arg |
| Glu | Trp | Thr | Lys 260 | Pro | Glu | Asn | Leu | Tyr 265 | Leu | Ala | Glu | Val | Asn 270 | Val | His |
| Leu | Pro | Arg 275 | Phe | Lys | Leu | Glu | Glu 280 | Ser | Tyr | Asp | Leu | Thr 285 | Ser | His | Leu |
| Ala | Arg 290 | Leu | Gly | Val | Gln | Asp 295 | Leu | Phe | Asn | Arg | Gly 300 | Lys | Ala | Asp | Leu |
| Ser 305 | Gly | Met | Ser | Gly 310 | Ala | Arg | Asp | Leu | Phe | Val 315 | Ser | Lys | Ile | Ile | His 320 |
| Lys | Ser | Phe | Val | Asp 325 | Leu | Asn | Glu | Glu | Gly 330 | Thr | Glu | Ala | Ala | Ala 335 | Ala |
| Thr | Ala | Gly | Thr 340 | Ile | Met | Leu | Ala | Met 345 | Leu | Met | Pro | Glu | Glu 350 | Asn | Phe |
| Asn | Ala | Asp 355 | His | Pro | Phe | Ile | Phe 360 | Phe | Ile | Arg | His | Asn 365 | Pro | Ser | Ala |
| Asn | Ile 370 | Leu | Phe | Leu | Gly | Arg 375 | | | | | | | | | |

MASPIN, A SERPIN WITH TUMOR SUPPRESING ACTIVITY

STATEMENT AS TO FEDERALLY SPONSORED RESEARCH

The invention described herein was made in part with the support of the U.S. Government (NIH grant nos. PO1 CA22427 and OIG CA39814 to Dr. Ruth Sager). The U.S. Government therefore has certain rights in the invention. This application is a continuation-in-part of currently U.S. Ser. No. 07/938,823 (herein incorporated by reference), which was filed Sep. 1, 1992, now abandoned, which was commonly owned with the present application, and which in turn is a continuation-in-part of U.S. Ser. No. 07/844,296, filed Feb. 28, 1992, now abandoned, which in turn is a continuation-in-part of U.S. Ser No. 07/662,216, filed Feb. 28, 1991, now abandoned.

BACKGROUND OF THE INVENTION

The field of the invention is tumor suppressor genes.

Cancer at the cellular level is characterized by the disruption of multiple regulatory mechanisms resulting from multiple genetic changes. The search for specific genes with major cancer-related effects has focussed on two fundamental processes: control of proliferation, and control of invasion and metastatic spread. Both processes are complex, and the relevant cancer-related changes in gene expression involve both increases and decreases in the activity of particular proteins.

Metastatic spread occurs when primary tumor cells invade into lymphatics and blood vessels, and disseminate to distant organs (Fidler et al., J. Natl. Cancer Inst. 82:166, 1990; Liotta et al., Cancer Res. 51:5054, 1991; Nicolson, Semin. Cancer Biol. 2:143, 1991; and Chen, Current Opin. Cell Biol. 4:802, 1992). The multiple steps involved in metastasis include proteolytic attack on the basement membrane and extracellular matrix (ECM), adhesion to endothelial cells leading to intravasation, and later extravasation from the circulatory system into tissues such as lung and bone in which the tumor cells are able to proliferate. In normal cells, these processes of invasion and metastasis are blocked by an intricate array of genetically programmed regulatory mechanisms. Overcoming these protective barriers to invasion and metastasis requires multiple changes in gene expression, resulting in gain or loss of gene functions that contribute to tumor progression.

Increased proteolytic activity augments invasion, as evidenced by the increased activity of serine proteases (Testa et al., Cancer Metastasis Rev. 9:353, 1990; Dano et al., Adv. Cancer Res. 44:139, 1985; Foekens et al., Cancer Res. 52:6101, 1992; Ossowsky, Cancer Res. 52:6754, 1992; Sumiyoshi, Int. J. Cancer 50:345, 1992; Duffy et al., Cancer Res. 50:6827, 1992; and Meissauer et al., Exp. Cell Res. 192:453, 1991, metalloproteases (Birkedal-Hansen (ed) Proceedings of the Matrix Metalloporteinase Conference, Destin, Florida, Gustav Fischer Verlag, 1990; Matrisian et al., Am. J. Med. Sci. 302:157, 1991; Stetler-Stevenson, Cancer Metastasis Rev. 9:289, 1990; DeClerck et al., Cancer Res. 52:701, 1992; Bassett, Nature 348:699, 1990; Wolf et al., Proc. Natl. Acad. Sci. USA 90:1843, 1993; and Sato et al., Oncogene 7:77, 1992), and cathepsins (Rochefort et al., Cancer Metast. Rev. 9:321, 1990; and Kobayashi et al., Cancer Res. 52:3610, 1992) in invasive tumor cells. The principal serine proteases known to be associated with tumor invasion mediate the plasminogen activation cascade. In this pathway, plasminogen is converted by plasminogen activators to plasmin, which is a wide-spectrum serine protease that degrades many components of the ECM directly, or indirectly via the activation of metalloproteases. The activity of the plasminogen activators is negatively regulated by plasminogen activator inhibitory proteins: PAI-1, PAI-2, and protease nexins (Chen, Current Opin. Cell Biol. 4:802, 1992).

The elevated expression of uPA (urokinase plasminogen activator) in breast carcinomas and other cancers has been reported by numerous investigators since the 1970's (Testa et al., Cancer Metastasis Rev. 9:353, 1990; Dano et al., Adv. Cancer Res. 44:139, 1985; Foekens et al., Cancer Res. 52:6101, 1992; Ossowsky, Cancer Res. 52:6754, 1992; Sumiyoshi, Int. J. Cancer 50:345, 1992; Duffy et al., Cancer Res. 50:6827, 1992; and Meissauer et al., Exp. Cell Res. 192:453, 1991; Heidtmann et al., Cancer Res. 49:6960, 1989; Sumiyoshi et al., Thromb Res. 63:59, 1991; Reilly et al., Int. J. Cancer 50:208, 1992, Cajot et al., Proc. Natl. Acad. Sci. USA 87:6939, 1990; Foucre et al., Br. J. Cancer 64:926, 1991; Shirasuna et al., Cancer Res. 53:147, 1993; and Janicke et al., Br. Can. Res. & Treat. 24:195, 1993). More recently, it has been shown that PAI-1 and PAI-2 are also elevated in malignancy (Sumiyoshi, Int. J. Cancer 50:345, 1992; Heidtmann et al., Cancer Res. 49:6960, 1989; Sumiyoshi et al., Thromb Res. 63:59, 1991; Reilly et al., Int. J. Cancer 50:208, 1992, Cajot et al., Proc. Natl. Acad. Sci. USA 87:6939, 1990; Foucre et al., Br. J. Cancer 64:926, 1991; Shirasuna et al., Cancer Res. 53:147, 1993; and Janicke et al., Br. Can. Res. & Treat. 24:195, 1993). These findings are inconsistent with the simple paradigm of protease/antiprotease balance in normal cells and its imbalance in tumor cells, thus confusing the issue of how effective uPA may be in metastatic dissemination. Recent studies of the uPA receptor and its importance in modulating uPA activity (Testa et al., Cancer Metastasis Rev. 9:353, 1990; Vassalli et al., J. Cell Biol. 100:86, 1985; and Lund et al., EMBO J. 10:3399, 1991) have indicated further levels of regulation. Thus, although it has been clearly established that uPA is capable of degrading components of the basement membrane and ECM, and that it is often elevated in advanced breast cancer, its precise role in breast cancer invasion remains to be established. Similarly, the importance of PAI-1 and PAI-2 in inhibiting breast cancer invasion is not clearly established (Testa et al., Cancer Metastasis Rev. 9:353, 1990).

The matrix metalloproteases (MMPs) include collagenases and stromelysins. The type IV collagenases (gelatinases), in particular the 72 kDa form, are active in tumor invasion, as indicated by elevated levels in aggressive human tumors (Stetler-Stevenson, Cancer Metastasis Rev. 9:289, 1990). The tissue inhibitors of metalloproteinase activity, TIMP-1 and TIMP-2, target the type IV collagenases, with TIMP-2 interacting exclusively with the 72 kDa form (Stetler-Stevenson et al., Annu. Rev. Cell Biol. 9:541, 1993). Stromelysins-1 (transin) and -2 have been associated with tumor progression in rodent systems, whereas a smaller molecule called PUMP has been identified in human tumor cells (Matrisian et al., Am. J. Med. Sci. 302:157, 1991). Extensive studies of stromelysin-3 have shown a strong correlation with advanced breast cancer (Bassett, Nature 348:699, 1990; Wolf et al., Proc. Natl. Acad. Sci. USA 90:1843, 1993). This protease is secreted by stromal fibroblasts that are proximal to invasive primary breast carcinomas, and not by the epithelial tumor cells, showing the importance of cell-cell interactions in tumorigenic mechanisms.

SUMMARY OF THE INVENTION

Disclosed herein is a new gene, originally isolated by subtractive hybridization, that is involved in protection against a primary step in the metastatic cascade. The gene, called maspin, encodes a novel serine protease inhibitor expressed in normal mammary epithelial cells in culture and in the normal breast. Its expression decreases during progression from well-differentiated to poorly differentiated primary carcinomas, and is absent in most lymph node and distant metastatic lesions. The inferred structure of the protein is consistent with serine protease inhibitor activity. Functional studies indicate that the protein has tumor suppressing and invasion suppressing activity.

The invention thus includes an isolated DNA encoding a polypeptide substantially identical to maspin (i.e., having at least 90% sequence identity to SEQ ID NO:2, with any amino acid substitutions preferably being conservative), or to an allelic variant of SEQ ID NO:2, or to a homolog of maspin from a species other than man. The isolated DNA preferably contains a DNA sequence which hybridizes under stringent conditions (as defined below) with the DNA sequence of SEQ ID NO:1, or the complement thereof, and may contain the sequence of SEQ ID NO:1. It is preferably incorporated into a vector (a virus, phage, or plasmid) which can be introduced by transfection or infection into a cell. The vector preferably includes one or more expression control sequences, in which case the cell transfected by the vector is capable of expressing the polypeptide. By "isolated DNA" is meant a single- or double-stranded DNA that is free of the genes which, in the naturally-occurring genome of the animal from which the isolated DNA is derived, flank the maspin gene. The term therefore includes, for example, either or both strands of a cDNA encoding maspin or an allelic variant thereof; a recombinant DNA which is incorporated into a vector, into an autonomously replicating plasmid or virus, or into the genomic DNA of a prokaryotic or eukaryotic cell; or a genomic DNA fragment (e.g., produced by PCR [polymerase chain reaction] or restriction endonuclease treatment of human or other genomic DNA). It also includes a recombinant DNA which is part of a hybrid gene encoding additional polypeptide sequence.

Stringent conditions for both DNA/DNA and DNA/RNA hybridization assays are as described by Sambrook et al., *Molecular Cloning, A Laboratory Manual,* 2nd Ed., Cold Spring Harbor Laboratory Press, Cold Spring Harbor, N.Y., 1989, herein incorporated by reference. For example, see page 7.52 of Sambrook et al.

Also within the invention is an isolated DNA at least 15 nucleotides in length (preferably at least 30, more preferably at least 100, and most preferably at least 500), including (a) a strand which hybridizes under stringent conditions to a DNA having the sequence of SEQ ID NO:1, (b) the complement thereof, or (c) a double stranded DNA including both (a) and (b). Multiple copies of this isolated DNA (useful, for example, as a hybridization probe or PCR primer) can be produced by recombinant means, by transfecting a cell with a vector containing this DNA.

The invention also includes a purified preparation of maspin protein (SEQ ID NO:2), or a fragment of maspin that is an antigenic polypeptide containing from 10 to 374 amino acid residues of maspin (preferably at least 12, more preferably at least 14, and most preferably at least 18 (e.g., 20 or more), which polypeptide fragment contains an epitope of maspin such that an antibody raised against the fragment (or against a conjugate of the polypeptide and keyhole limpet hemocyanin) forms an immune complex with maspin itself.

Such an antibody may be either polyclonal or monoclonal, and is generated by standard methods including the step of immunizing an animal with an antigen containing an antigenic portion of maspin. Also within the invention are hybrid polypeptides containing (1) maspin or an antigenic fragment thereof, covalently attached to (2) a second polypeptide. Such hybrid polypeptides can be made by any of a number of standard techniques well known to those of ordinary skill, including recombinant methods, in which case the covalent attachment is a peptide bond, or chemical conjugation, in which case the covalent attachment is another type of bond, such as a disulfide bond. Linking maspin or an antigenic fragment thereof to a second polypeptide provides a means for readily isolating the hybrid from a mixture of proteins, by the use of an affinity column to which the second polypeptide (e.g., glutathione transferase) binds directly. Such hybrid polypeptides may also have the advantage of increased immunogenicity relative to maspin or the maspin fragment, so that antibodies are more readily obtained.

Both the isolated DNAs of the invention and the antibodies of the invention are useful in diagnostic methods for detecting carcinomas, or for staging a carcinoma, where the suspected carcinoma is derived from a type of cell which normally expresses the maspin gene to a significant and easily detectable degree (e.g., mammary epithelial cells). One such diagnostic method includes the steps of providing a test cell (e.g., in the form of a tissue section or a cell preparation) from a given type of epithelial tissue; contacting the mRNA of the test cell with a nucleic acid probe containing a sequence antisense to (i.e., complementary to) the sense strand of) a segment of SEQ ID NO:1, which segment is at least 15 (preferably at least 20, more preferably at least 30, even more preferably at least 40, and most preferably at least 100) nucleotides in length; and comparing (1) the amount of hybridization of the probe to the mRNA of the test cell, with (2) the amount of hybridization of the probe to the mRNA of a normal control (i.e., non-cancerous) cell from the same type of epithelial tissue, wherein an amount of hybridization to the mRNA of the test cell substantially less than the amount obtained with the mRNA of the normal control cell (preferably less than about one-half, more preferably less than about one-third, and more preferably less than about one-tenth the control amount of hybridization) is an indication that the test cell is cancerous. An absence of hybridization with the mRNA of the test cell is an indication that the test cell is from an advanced, probably metastatic tumor, while an amount of hybridization that is detectable but substantially less (e.g., one-third or less) than that measured in a normal cell of the same tissue type is an indication that the test cell is from an early stage carcinoma that is probably not yet metastatic. The assay can be conveniently carried out using standard techniques of in situ hybridization or Northern analysis.

The antibody-based assays of the invention are comparable to the above. The proteins of the test cell, or from a fluid bathing the test cell, are contacted with an antibody (polyclonal or monoclonal) specific for maspin, and the amount of immunocomplex formed with such proteins is compared with the amount formed by the same antibody with the proteins of a normal control cell (or from a fluid bathing the normal control cell) from the same type of epithelial tissue as the test cell. An amount of immunocomplex observed with the proteins of the test cell substantially less than the amount observed with the proteins of the normal control cell (e.g., less than about one-half, preferably less than about one-third, and more preferably less than about one-tenth) is an indication that the test cell is cancerous. The absence of consistently detectable immunocomplex formed with the proteins of the test cell is an indication that the test cell is from an advanced, probably metastatic tumor, while an amount of immunocomplex formation that is consistently detectable but less (e.g., one-third or less) than that measured in a normal cell of the same tissue type is an indication that the test cell is from an early stage carcinoma that is probably not yet metastatic. (By consistently detectable is meant that, in all or nearly all of repeated trials, an amount greater than the applicable background level is observed.)

The immunoassay of the invention alternatively can be carried out on a biological fluid, since maspin protein is normally secreted by epithelial tissues such as mammary tissue. Such an assay would require obtaining a sample of a biological fluid (e.g., blood, serum, urine, saliva, milk, ductal fluid, tears, or semen) from an individual, which biological fluid would, in an individual free of carcinoma, contain a control amount of maspin. The sample, or protein derived from the sample, is contacted with the anti-maspin antibody, and the amount of immunocomplex formed is determined. This amount indicates the concentration or amount of maspin in the biological fluid. When compared to a sample previously or subsequently obtained from the same individual, this method provides a way to monitor the appearance, progress, or treatment of a carcinoma.

In another aspect, the invention features a method for screening candidate anticancer compounds, using as a screening tool cells (e.g., primary cells or an established cell line) from a carcinoma derived from a given tissue type in which the maspin gene is intact but down-regulated: that is, the level of expression of maspin in that carcinoma is significantly lower than (e.g., less than one-third of) the level of expression in normal epithelial cells from that type of tissue. The tissue may be from a human or another animal, and is preferably mammary epithelium. It is preferred that there be no detectable expression of maspin in the cells to be employed in the screen: i.e., the maspin gene is entirely shut down. The screening method includes the step of providing two samples of the screening cells, one of which is treated with a candidate anticancer compound and the other of which serves as control. The level of expression of maspin in the treated sample is compared with the level in the second sample, a higher level in the first sample being an indication that the candidate compound is a potential anticancer agent. The level of expression can be determined by use of hybridization methods or by immunoassay, as described herein.

As an alternative way of screening for potential anticancer agents, one can use any cell in which expression of maspin is undetectable, but which contains an intact maspin gene. This cell would be treated with a candidate anticancer compound, and a determination made of whether expression of maspin is thereby increased in the cell. Such an increase of maspin expression is an indication that the candidate compound is a potential anticancer agent. As above, the level of expression can be determined by use of hybridization methods or by immunoassay.

Also within the invention are methods of treating a carcinoma, where the carcinoma is one in which expression of maspin is decreased relative to normal cells of the tissue type from which the carcinoma cells were derived. In these methods, the patient is treated with an effective amount of a compound which increases the amount of maspin in, or in the immediate vicinity of, his or her carcinoma cells. This compound could be, for example, maspin or a biologically active fragment thereof; a nucleic acid encoding maspin and having expression control elements permitting expression in the carcinoma cells; or an agent which increases the level of expression of a maspin gene endogenous to the carcinoma cells (i.e., which up-regulates expression of the maspin gene).

The invention also features methods for in vivo screening of candidate anticancer agents, or for determining whether a particular carcinoma, in which maspin expression is down-regulated in comparison with normal cells of the same tissue type, is treatable with a given compound that increases expression of maspin. Such a method would include the steps of (1) introducing a carcinoma cell (e.g., a from a mammary carcinoma) into a severely immunodeficient animal (e.g. a nude mouse), the expression of maspin (SEQ ID NO:2) in the cell being down-regulated in comparison with that in a normal cell of the same type of tissue as the carcinoma cell; (2) treating the animal with a compound which increases the concentration of maspin in or around (i.e., in the immediate vicinity of) the carcinoma cell; and (3) determining whether this treatment affects the rate of proliferation or metastasis of the carcinoma cell in the animal, wherein a decrease in the rate of proliferation or metastasis in the presence of the compound is an indication that (a) the compound is potentially useful for treatment of carcinomas, and (b) the carcinoma from which the cell is derived is potentially treatable with the compound.

Besides the in vivo assay described above, one can also utilize an in vitro assay for carcinoma cell invasive capacity based upon the assay described in detail below. Such an assay would include the steps of (1) providing a first and a second carcinoma cell, which cells express maspin (SEQ ID NO:2) to a degree substantially lower than (i.e., less than one-third of, when measured by hybridization to cellular mRNA) that of a normal cell from the same type of tissue as said carcinoma cells; (2) treating the first cell with a compound which increases the concentration of maspin (SEQ ID NO:2) in or around the first cell; and (3) comparing the invasive capacity of each of the first and second cells in an in vitro assay such as that described below, wherein a decrease in invasive capacity of the (treated) first cell relative to that of the (untreated) second cell is an indication that (a) the compound is potentially useful for treatment of carcinomas, and (b) the carcinoma from which the cells are derived is potentially treatable with the compound. This assay is also useful for detecting maspin activity in a biological sample (e.g., during the process of purification of maspin, or for testing the biological activity of maspin fragments or derivatives, or for determining the presence of maspin in a sample of blood, milk, or other biological fluid), wherein a decrease in invasive capacity of the (treated) first cell relative to that of the (untreated) second cell is an indication that maspin, or maspin biological activity, is present in the sample.

Other features and advantages of the invention will be apparent from the following detailed description, and from the claims.

BRIEF DESCRIPTION OF THE DRAWINGS

FIG. 3 is a representation of the complete cDNA and predicted amino acid sequence of maspin (SEQ ID NO:1). cDNA sequencing was performed using ABI 373A Automated DNA Sequencer at the core facility of Dana-Farber Cancer Institute. The polyadenylation signal is underlined.

FIG. 4 is a comparison of the amino acid sequence of maspin (SEQ ID NO:2) with that of other serpins. Identical residues are boxed. Three regions used for antibody production are underlined. The arrow denotes the proposed reactive center of maspin. At, α1-antitrypsin (SEQ ID NO:3); ei, human monocyte/neutrophil elastase inhibitor (SEQ ID NO:4); ovalbu, ovalbumin (SEQ ID NO:5); pai1, human plasminogen activator inhibitor type 1 (SEQ ID NO:6); pai2, human plasminogen activator type 2 (SEQ ID NO:7); serapin, horse serapin (SEQ ID NO:8).

FIGS. 6A–F are photographs of tissue sections stained by immunoperoxidase to illustrate maspin protein expression in acetone-fixed normal mammary epithelial cell cultures (FIG. 6A), and in formalin-fixed paraffin embedded sections of benign (FIG. 6B) and carcinomatous breast tissue (FIG. 6C, ductal carcinoma in situ; FIGS. 6D and 6E, invasive ductal carcinomas; FIG. 6F, pleural effusion containing metastatic breast cancer). Maspin-immunoreactive sites were unmasked in formalin-fixed sections by pretreatment of the sections in 10% sucrose at 80° C. for 2 hours. Both cell cultures and tissue sections were incubated with 5 μg/ml of AbS4A followed by immunoperoxidase detection employing biotinylated tyramine (Adams, J. Histochem. Cytochem 40:1457, 1992). 3-Amino-9-ethylcarbazole was used as the chromogen and nuclei were counterstained with Mayer's hematoxylin. Presorbtion of the primary antibody AbS4A with immunizing peptide eliminated all specific maspin staining. Key: sm, secreted maspin; L, luminal cell; myo, myoepithelial cell; f, fibroblast; dcis, ductal carcinoma in situ; idc, invasive ductal carcinoma; nd, normal benign breast duct; pe, pleural effusion.

FIG. 7 is a Western analysis of maspin in MDA-MB-435 transfectants. Maspin was detected by peptide affinity purified antibody AbS1A. Lanes 1–5, neo transfected; lanes 6–12, maspin transfectant clones T1, T4, T5, T6, T7, T2 and T3, respectively.

DETAILED DESCRIPTION

IDENTIFICATION OF MASPIN

Figure 1:
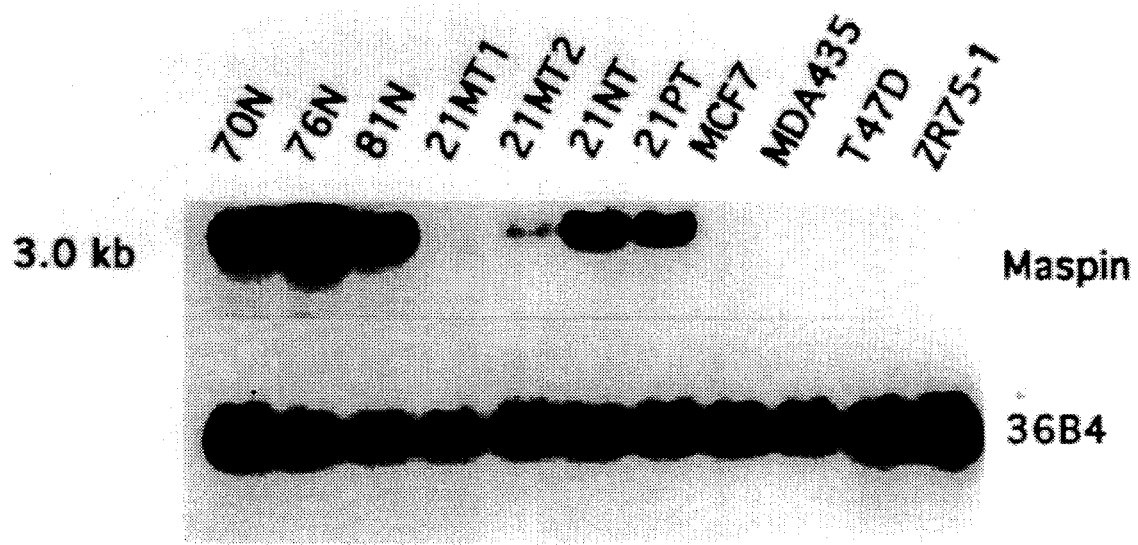
FIG. 1 is a Northern blot analysis of maspin expression in normal and tumor cells. Total cellular RNA was isolated from exponentially growing cells cultured in DFCI-1 medium (Band et al., Proc. Natl. Acad. Sci. USA 86:1249, 1989). 20 ug RNA was electrophoresed on 1% formaldehyde agarous gel, transferred to nylon membrane and hybridized with $^{32}$P-labeled maspin probe. Lanes 1–3, normal breast epithelial cells 70N, 76N, 81N; lanes 4–11, breast tumor cells 21MT1, 21MT2, 21NT, 21PT, MCF7, MDA-MB-435, T47D, and ZR75-1.
Figure 2:
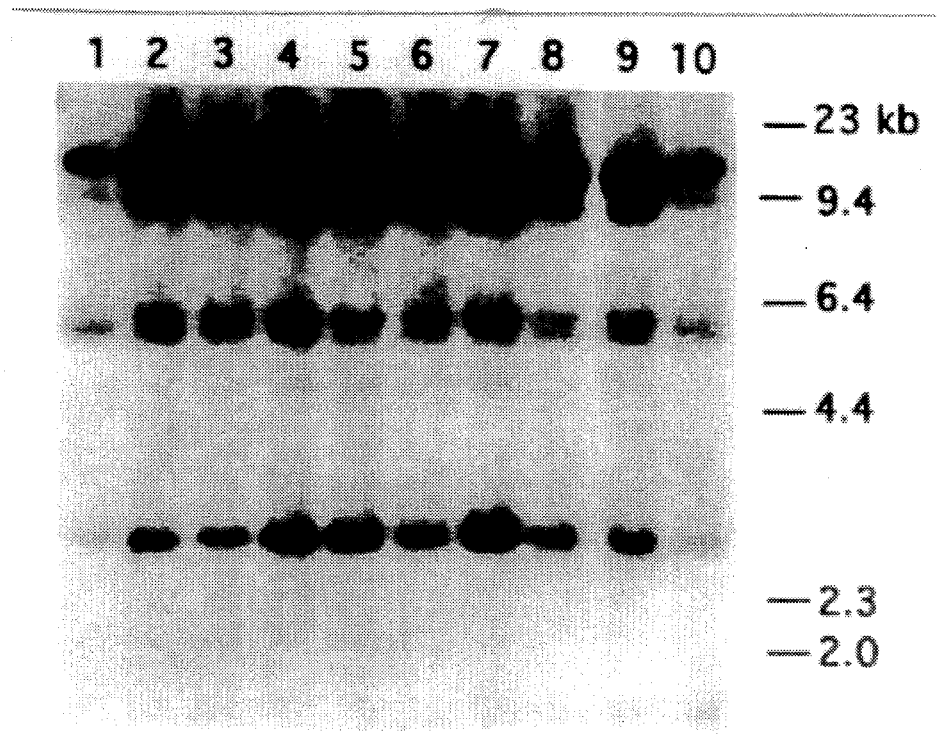
FIG. 2 is a Southern blot analysis of the maspin gene. DNA (20 mg) was digested with XbaI, fractionated on 1% agarose gel and transferred to nylon membrane. The blot was hybridized with $^{32}$P-labeled full length maspin cDNA. Lanes 1–2, normal breast cell 70N and 76N; lanes 3–10, breast tumor cell lines 21MT1, 21MT2, 21NT, 21PT MDA-MB-231, MDA-MB-435, MCF7, ZR75-1.

Using subtractive hybridization (as described in U.S. Ser. No. 07/844,296), a new member of the serpin family has been isolated, cloned, sequenced, and partially characterized. The gene was named maspin because of its sequence similarity to other serpins, and its initial identification in mammary epithelial cells. As shown in FIG. 1, the maspin gene expresses a single 3.0 kb mRNA in three normal mammary epithelial cell strains (Band et al., Proc. Natl. Acad. Sci. USA 86:1249, 1989) but not in a series of tumor cell lines including those shown in FIG. 1 as well as MDA-MB-157, MDA-MB-231, MDA-MB-436, MDA-MB-468, BT549, and HS578T (not shown). Two cell lines from primary tumors of a single patient (21PT and 21NT) (Band et al., Cancer Res. 50:7351, 1989) expressed maspin mRNA, but at a much reduced level compared with the normal cells. Neither foreskin fibroblasts nor breast-derived fibroblasts expressed detectable maspin mRNA. Southern analysis of DNA from normal and tumor cells (FIG. 2) using the restriction enzyme XbaI, which produced 5 fragments that hybridized with the maspin probe, showed no differences in pattern among them. Thus the gene is present and unaltered at this level of resolution in the tumor cell lines including the 21T series, in which the primaries (21PT, 21NT) express the mRNA and the cells of metastatic origin do not. This evidence suggests that maspin is a Class II candidate tumor suppressor gene, down-regulated but not mutated in cancer cells (Lee et al., Proc. Natl. Acad. Sci. USA 88:2825, 1991; Sager et al., FASEB J. 7:964–970, 1993)

Maspin cDNA (SEQ ID NO:1) was isolated from a normal human mammary epithelial cell library (76N), as described in U.S. Ser. No. 07/844,296. The cDNA sequence contains 2584 nucleotides with a polyadenylation signal located 16 nucleotides from the 3' terminus of the sequence, as shown in FIG. 3. The full length sequence includes 75 nucleotides of the 5' untranslated region and 1381 nucleotides of 3' untranslated region. The initiation codon and surrounding nucleotides fit the Kozak consensus (Kozak, Nucleic Acid Res. 12:857, 1984). The cDNA encodes a protein of 375 amino acids with an N-terminal methionine and C-terminal valine. Maspin also contains 8 cysteine residues, and may utilize two or more disulfide bonds to stabilize its tertiary structure.

Multiple alignment studies based on data base searches using BLAST at the National Center for Biotechnology Information and analyzed by the GCG Pileup program demonstrate close homology to the serpin superfamily of serine proteinase inhibitors (see FIG. 4). Serpins are a diverse family of proteins related by virtue of primary sequence homology spanning the entire length of each molecule, and varying from 15–50% at the amino acid level and higher at the DNA level. Maspin exhibits closest homology at the protein sequence level to the equine (43%) and human neutrophil-monocyte elastase inhibitors (39%), human PAI-2 (31%), human squamous cell carcinoma antigen (SCCA, 34%), and chicken egg albumin (31%).

THE SERPIN FAMILY

Serpin molecules possess important physiological functions, including proteinase inhibition (inhibitors of complement activation, coagulation, kinin formation, and fibrinolysis), hormone transport (thyroxine binding globulin, cortisol binding globulin), vasoactive peptide donors (angiotensinogen), and unknown function (ovalbumin) (for reviews see Travis et al., Biol. Chem Hoppe-Seyler 371:3, 1990; Huber et al., Biochem. 28:1, 1989).

The crystallographic structures have been solved for native and cleaved ovalbumin, cleaved α1-antitrypsin, cleaved α1-antichymotrypsin, and latent plasminogen activator inhibitor-1 (Stein et al., Nature 347:90, 1990; Wright et al., J. Mol. Biol. 213:513, 1990; Loebermann et al., J. Mol. Biol. 177:531, 1984; Baumann et al., J. Mol. Biol. 218:595, 1991; Mottonen et al., Nature 355:270, 1992). In each case, the structures have proven to be very similar, indicating a conserved molecular framework. These studies confirm the usefulness of molecular modeling to make predictions concerning the unsolved structures of other serpins.

Active inhibitory serpins (S-form) interact with their target proteases with a 1:1 stoichiometry to form stable, denaturation-resistant complexes, in which the protease is inactive. Of primary importance in determining the specificity of the target protease is the nature of the $p_1$ residue of the reactive center. Serpins with Ala, Val, or Met at the $p_1$ position are inhibitors of elastase-like proteinases, while serpins with Arg at the $p_1$ position inhibit trypsin-like proteases.

The alignment of maspin with other serpins (FIG. 4) provides preliminary evidence that maspin may also function as a proteinase inhibitor. The homology alignment identifies Arg as the putative $p_1$ residue in maspin, suggesting that it may inhibit trypsin-like proteases such as plasmin, uPA, and tPA. Because of the gap preceding the reactive site peptide bond, other alignments are possible, but each likely alignment provides a $P_1$ residue with the potential for generating inhibitory activity.

IDENTIFICATION OF MASPIN PROTEIN USING ANTI-MASPIN ANTIBODIES

Figure 5A:
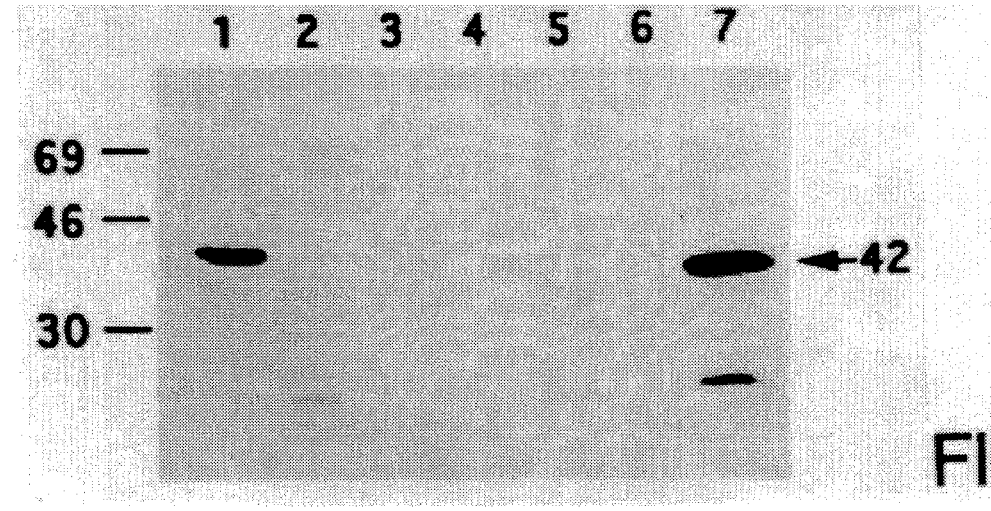
FIG. 5A is a Western blot analysis of maspin protein from normal and tumor cells. Cells were lysed in SDS-loading buffer, and extracts were electrophoresed on 10% SDS gel and transferred on to Immobilon membrane. Maspin was detected by antiserum AbS1A using the ECL system. Lane 1, 76N; lanes 2–5, tumor cells MCF7, MDA-MB-435, ZR75-1; lane 6, MDA-MB-435 neo transfectant; lane 7, MDA-MB-435 maspin transfectant.
Figure 5B:
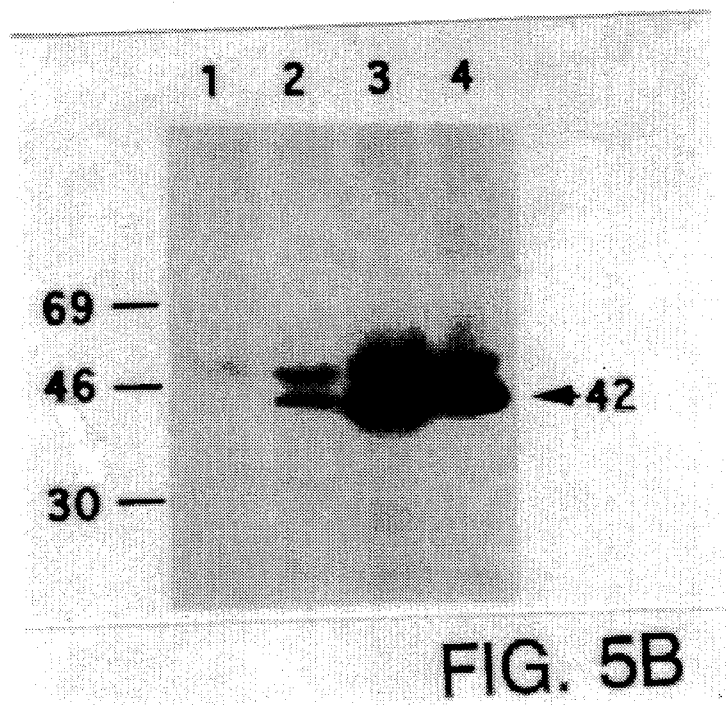
FIG. 5B is a Western blot showing detection of maspin protein in normal cells, using immunoprecipitation. Growing normal cells (70N) were labeled with an $^{35}$S-labeled mixture of methionine and cysteine, and immunoprecipitated with on of four anti-maspin antibodies (lane 1, preimmune serum; lane 2, AbS3A; lane 3, AbS4A; lanes 4, AbS1A).

Three poorly conserved sequences (underlined in FIG. 4 as S1A, S3A, and S4A) were selected as the basis for designing synthetic oligopeptides for polyclonal antibody production, using conjugation to keyhole limpet hemocyanin [Harlow et al., Antibodies, A Laboratory Manual, Cold Spring Harbor Laboratory, N.Y., 1988 (Chapter 8)]. The antisera were respectively designated as AbS1A, AbS3A and AbS4A. AbS4A recognizes the reactive center loop encompassing the putative p1–p1' residue. As shown in FIG. 5A, a 42 kDa band was detected on a reducing SDS gel, both in normal cells (70N; lane 1) and in tumor cells (MDA-MB-435) transfected with maspin cDNA (lane 7). This molecular weight is consistent with the estimated size based on the primary sequence. All three antibody preparations reacted with this 42 kDa protein. No protein was detected in breast tumor cell lines MCF7, MDA-MB-468, MDA-MB-435, and ZR75-1, or in MDA-MB-435 transfected with control vector (lanes 2–6). All three antisera precipitated a 42 kDa band from normal cell extracts (FIG. 5B). These results demonstrate that the maspin gene encodes a 42 kDa protein present in normal mammary epithelial cells and absent in tumor cell lines that do not express the mRNA.

MASPIN EXPRESSION IN BENIGN AND MALIGNANT BREAST

Indirect immunofluorescence microscopy of a normal human mammary epithelial cell strain (76N) demonstrated that maspin protein is localized mainly to the pericellular space, with weak staining in the cytoplasm (FIG. 6A). These results demonstrate that maspin is secreted into the ECM, and may interact with its target protease in the ECM and/or on the plasma membrane. Primary mammary tumor cells grown in culture (21PT) exhibited weak staining with a pattern similar to the normal cells, consistent with their low-level expression of maspin mRNA (FIG. 1), whereas MDA-MB-435 cells were negative. Each of the maspin antisera AbS1A, AbS3A, and AbS4A generated similar staining patterns that could be preabsorbed by the corresponding immunizing peptide.

As shown in FIGS. 6A and B, acetone-fixed cryosections and formalin-fixed, paraffin-embedded sections of benign breast tissues (n=6) and benign epithelium adjacent to invasive carcinomas were maspin positive when immunostained with AbS4A. Maspin expression was particularly intense in myoepithelial cells, both within large ducts and terminal duct lobular units (TDLU). Luminal epithelial cells were heterogeneously positive (often showing weak granular cytoplasmic immunopositivity of some cells), with more intense apical reactivity and some positivity of intraluminal secreted material (FIG. 6B). Inflammatory and stromal cells were always negative.

Figure 9:
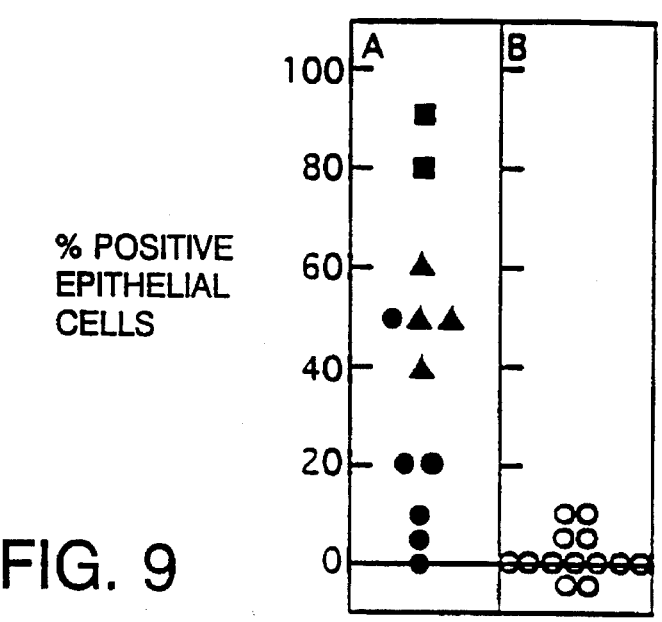
FIG. 9 is a chart illustrating the reactivity of AbS4A antiserum with several mammary carcinoma samples. Affinity-purified AbS4A (at 5 μ/ml) was reacted with formalin-fixed 5 μm paraffin-embedded sections that were pretreated in 10% sucrose at 80° C. for 1 hour. Antibody-antigen complexes were visualized by the modified immunoperoxidase method using biotinylated tyramine (Adams, J. Histochem. Cytochem. 40:1457, 1992). The % positive cells denotes the number of carcinoma cells that were reactive with AbS4A divided by the total number of tumor cells×100 in (A) primary breast carcinomas, and (B) mammary lymph node metastases and pleural effusions (o). Each symbol represents a specimen from a different individual. Many tumor cells in ductal carcinomas in situ (■) expressed maspin. Differentiated components of invasive breast carcinomas (▲) expressed some maspin. Poorly differentiated neoplasms (●) failed to exhibit maspin immunoreactivity.

Twelve invasive carcinomas of the breast, eleven regional lymph node metastases, two pleural effusions containing metastatic breast cancer, and adjacent in situ epithelial elements were also evaluated for maspin expression (FIG. 9). Carcinoma in situ was weakly immunopositive, and apical expression was occasionally noted. Maspin expression was highest within myoepithelial cells (adjacent to the basement membrane). Secreted maspin was sometimes observed in the luminal space of benign breast (FIG. 6B) and ductal carcinomas in situ (FIG. 6C), and rarely in invasive ductal carcinomas, as for example in the well-differentiated tubular variant (FIG. 6D). Most malignant cells in invasive carcinomas failed to express maspin (FIG. 6E), but a minority of cells in well differentiated tumors expressed maspin focally (FIG. 9). Maspin was undetectable or very weakly expressed in all lymph node metastases and pleural effusions examined (FIG. 6F). These findings suggest a biological role for maspin in the benign breast and a potentially pivotal alteration in maspin expression during the progression of breast cancer.

DECREASED GROWTH IN NUDE MICE OF TUMOR TRANSFECTANTS EXPRESSING MASPIN

Tumor cell line MDA-MB-435 forms tumors at the site of orthotopic injection and metastasizes in nude mice (Price et al., Cancer Res. 50:717, 1990). To investigate whether maspin has inhibitory effects on tumor formation in nude mice, MDA-MB-435 cells were transfected with an expression vector encoding maspin under the control of the CMV promoter (Tomasetto et al., J. Cell Biol. 122:157, 1993). The exogenous gene expressed a 3.0 kb mRNA and a 42 kDa protein at levels similar to those seen in normal cells, whereas no maspin was expressed by the neo-controls (FIG. 7). The low levels of maspin in transfected clones T2 and T4 resulted from instability in maspin transfectants. In cell culture, the maspin transfectants, the neo-controls, and the MDA-MB-435 parental cells all grew at the same rate in alpha-MEM medium containing 5% fetal calf serum (data not shown).

Four maspin transfectants and two vector control transfectants were tested in nude mice as described (Price et al., Cancer Res. 50:717, 1990). Table 1 summarizes the results obtained from two duplicate experiments. At 10 weeks post-inoculation, all mice were sacrificed, and their tumors excised and weighed. Between 6 and 10 weeks, some mice died due to tumor burden or illness. These mice are not included in Table 1. Three of the four maspin transfectant clones produced much smaller tumors than the vector control clones, whereas one clone (T1) grew at the same rate as MDA-MB-435 and the neo-controls. Using the Student t-test, the differences between maspin transfectants and neo-controls were significant whether or not T1 was included in the calculations.

These results show unequivocally that maspin expression leads to growth inhibition of injected transfectants compared with controls. It is obvious by inspection that T1 is not inhibited, whereas the other three transfectants are strongly inhibited. The inhibitory effect of maspin on tumor growth is not unexpected, since other laboratories have reported effects of proteases in inducing growth factor expression indirectly, perhaps via cleaved components of the ECM (Testa et al., Cancer Metastasis Rev. 9:353, 1990).

DECREASED INVASIVE CAPACITY OF MASPIN TRANSFECTANTS

Figure 8:
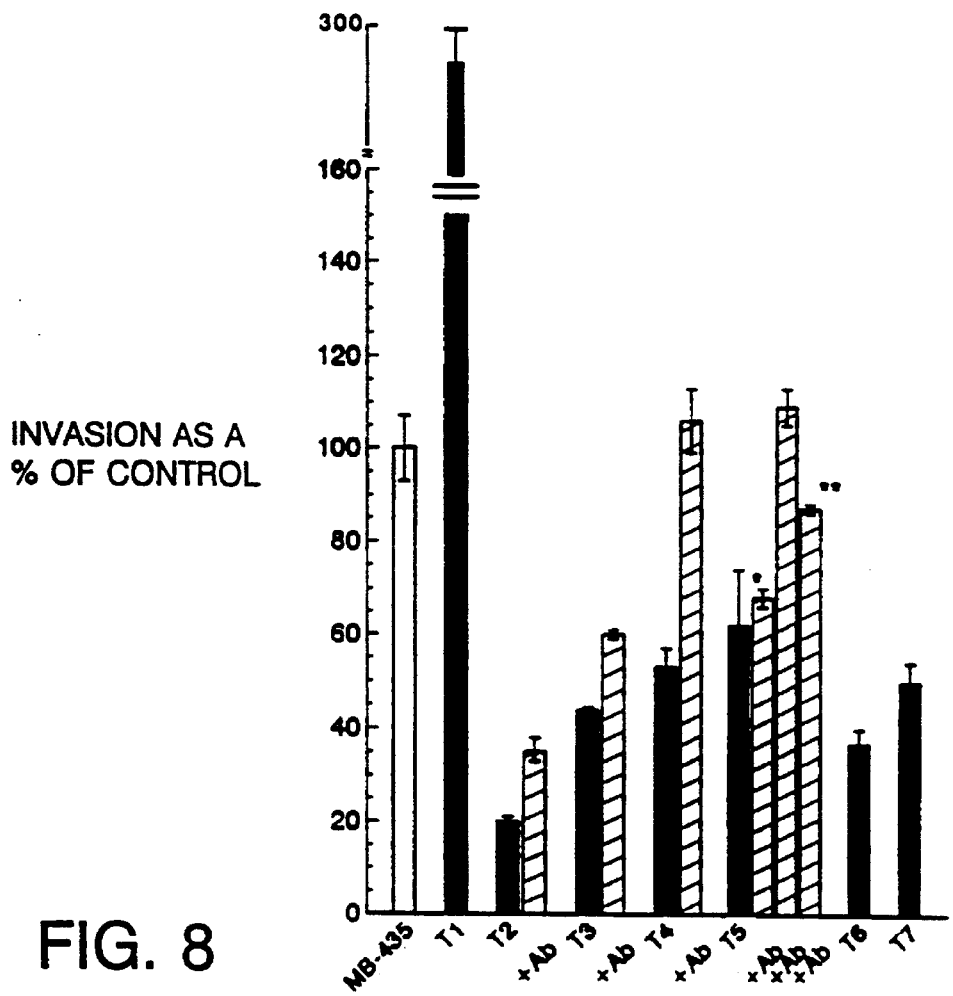
FIG. 8 is a bar graph illustrating the effect of maspin transfection into MDA-MB-435 cells on invasive potential in vitro in the presence or absence of antibodies to maspin. The invasive ability of maspin-transfected clones (T1–T7) to penetrate reconstituted basement membrane-coated (Matrigel; Becton Dickinson, Boston, Mass.) polycarbonate filters (containing 10 mm pores) was measured over 72 h using the Membrane Invasion Culture System (MICS). 1×10$^5$ cells were seeded into the upper wells of the MICS chamber onto the Matrigel-coated filter in DMEM medium containing 10% NuSerum (Becton Dickinson). After 72 h incubation at 37° C. with constant $O_2$ and $CO_2$ exchange, the cells that invaded the filter were collected, stained and counted with the aid of a light microscope. The invasion data of the non-transfected MDA-MB-435 cells were normalized to 100%, and the invasion data of the experimental and control transfectants are expressed as a percentage of this control. The data represent the average of two separate experiments; error bars represent the standard error of the mean and are based on n=6 for each experiment. To neutralize the activity of secreted maspin, selected clones were pretreated with AbS4A maspin antibody continuously during the course of the invasion assay at a concentration of 1.0 mg/ml, unless stated otherwise. In selected experiments, additional concentrations of the antibody were tested: *0.1 and **3.0 mg.ml. The invasive potential of the untreated clones was normalized to 100%, and the invasive potential of the treated clones is indicated as a percentage of the untreated respective clones.

An in vitro assay of tumor cell invasion through reconstituted basement membrane matrix (Matrigel) has been used to assess the functional activity of maspin (Hendrix et al., Cancer Letters 38:137, 1987). Seven maspin transfectant clones and 5 neo vector transfectant clones were compared with the parental MDA-MB-435 cells. Six (T2–T7) of the 7 maspin transfectant clones showed reduced invasive ability; as shown in FIG. 8, this difference was neutralized in a dose-dependent manner with the peptide affinity-purified antibody AbS4A. The antibody blocked the inhibitory effect of the recombinant maspin produced by the transfected cells, resulting in elevated invasive activity. Since AbS4A recognizes the reactive center of the protein, it is likely that the site of interaction with the target protease was blocked.

By immunofluorescence microscopy, we noted that maspin expression was heterogeneous in the pre-invasion cells. However, in the post-invasion cells, staining revealed that more than 95% were maspin-negative. Thus, the effectiveness of maspin in inhibiting invasion is somewhat underestimated in these experiments, owing to heterogeneity of expression in the transfectant population. Furthermore, our evidence that only the maspin-negative cells crossed the Matrigel barrier further demonstrates that the cells expressing maspin were inhibited in their ability to invade.

In addition, five neo-control transfectants were tested for their invasive capacity (data not shown). Of these, two expressed invasive activity comparable to the parental cells, whereas three of them showed a decrease in invasive activity. However, none of the five neo-controls responded to the AbS4A antibody, indicating that maspin was not responsible for the decreased invasiveness of the controls. This result is consistent with the absence of maspin protein in the neo-controls, as shown in FIG. 5A. In light of Liotta's three-step invasion model (Liotta et al., Cancer Res. 51:5054, 1991) (i.e., adhesion, degradation, and motility), the adhesive ability of all 12 transfectants (7 containing maspin and 5 controls) to Matrigel matrix were examined; no differences among them were found (data not shown).

These data support the hypothesis that the activity of maspin is associated with the inhibition of tumor cell invasive potential. It is noteworthy that the same transfectant clone (T1) which showed no inhibition of invasive potential in the invasion assay, also showed no decrease of tumor size when tested in the nude mouse assay. This clone, which is more invasive than the parental tumor cells, may overexpress a novel protease, and merits further investigation.

CHROMOSOMAL LOCATION OF MASPIN

A panel of 24 human-rodent somatic cell hybrids was used to map the chromosomal location of the maspin gene. All hybrids retained a single human chromosome except one line that contained both chromosome 20 and a low percent of chromosome 4, and one that contained both chromosomes 1 and X. In human DNA, the maspin probe detected a major 5.4 kb HindIII fragment, which was clearly resolved from a weakly hybridizing Chinese hamster fragment of about 20 kb. The presence of the 5.4 kb human maspin sequence in the hybrid clones correlated only with the presence of human chromosome 18 (Table 2). Only one of the 24 hybrids analyzed was positive for maspin; this hybrid contained chromosome 18 as the sole human DNA. No discordancies for localization to chromosome 18 were found, whereas there were at least two discordancies for localization to any other chromosome. The maspin gene has been localized to 18q21.3, the same chromosomal region as a closely related gene, PLANH2, that encodes plasminogen activator inhibitor-2 (PAI-2) (LeBeau et al., Human Gene Mapping 11, Cytogenet. Cell Genet. 58:739, 1991).

Example 1

Recombinant maspin

Using the information provided above, one of ordinary skill can generate a synthetic DNA probe consisting of a 20-nucleotide segment of the maspin cDNA sequence (SEQ ID NO:1), and use that probe to screen at high stringency a cDNA library from an appropriate epithelial cell line such as MCF7. Alternatively, one could design two appropriate PCR primers, based upon the disclosed cDNA sequence, and generate a maspin cDNA either from the same library, or directly from the mRNA of that cell line. Both of these procedures are standard ones readily carried out by one of ordinary skill in the art. Sequencing of the cDNA so obtained will confirm that it is the maspin cDNA disclosed herein. Multiple copies of the cDNA are readily produced by inserting the cDNA into a recombinant vector, and using that vector to transfect a prokaryotic host such as E. coli. This cDNA, or a fragment thereof, can be used to screen epithelial cell cDNA libraries from species other than human [e.g., mammalian species such as mouse, rat, guinea pig, hamster, rabbit, cow, pig, horse, sheep, monkey, and ape; or non-mammalian animals such as birds or insects (e.g., Drosophila); or microorganisms such as yeast] in order to identify the maspin homologs in such other species. It is likely that the stringency of the hybridization conditions would have to be adjusted to take into account the probable lack of complete sequence identity with the human cDNA.

Once the desired maspin cDNA is in hand, it can be inserted into an expression vector and used in an appropriate expression system to generate recombinant maspin protein. The expression system can be any standard system, including prokaryotic (e.g., E.coli), eukaryotic (e.g., yeast, CHO cells, COS cells, or baculovirus in insect cells), or cell-free. Since the protein appears to be secreted, it can be collected from the culture filtrate of E. coli, or from the medium bathing the transfected insect or other eukaryotic cells. Standard methods of protein purification, optionally including passage over an immunoaffinity column, can be employed to isolate the recombinant protein.

Example 2

Diagnostic Assay Utilizing Hybridization Probe

As described above, a nucleic acid probe containing some or all of the maspin-encoding sequence of the invention (SEQ ID NO:1) can be used to detect maspin mRNA in a sample of epithelial cells (e.g., a tissue section) suspected of being cancerous. The probe used would be a single-stranded DNA or RNA (preferably DNA) antisense to the coding sequence shown in FIG. 3. It could be produced by synthetic or recombinant DNA methods, and labelled with a radioactive tracer or other standard detecting means. The probe could include from 15 to the full 1125 nucleotides of coding sequence, and preferably is at least 30 nucleotides long. The assay can be carried out by standard methods of in situ hybridization or Northern analysis, using stringent hybridization conditions. Control hybridization assays can be run in parallel using normal epithelial cells or tissue sections from the same type of tissue as the test sample, and/or cells from a known carcinoma or carcinoma-derived cell line, or a cancer-containing tissue section. Cells which exhibit a substantially decreased level, or absence, of hybridization to the probe, compared to the level seen with normal epithelial cells, are likely to be cancerous. The amount of hybridization can be quantitated by standard methods, such as counting the grains of radioactivity-exposed emulsion on an in situ hybridization assay of a biopsy slide, or by densitometric scan of a Northern blot X-ray film. Alternatively, comparison of the test assay results with the results of the control assays can be relative rather than quantitative, particularly where the difference in levels of hybridization is dramatic. This assay is useful for detecting cancerous cells in breast epithelial tissue or in any other type of tissue in which maspin is normally expressed.

Example 3

Diagnostic Assay Utilizing Antibody Probe

Antibodies specific for maspin can be generated by standard polyclonal or monoclonal methods, using as immunogen a purified, naturally-occurring maspin; recombinant maspin; or any antigenic fragment of maspin which induces antibodies that react with naturally-occurring maspin. The latter fragment can be produced by synthetic or recombinant methods, or by proteolytic digestion of holo maspin. (Three examples of fragments useful for antibody production are described above.) If desired, the antigenic fragment can be linked by standard methods to a molecule which increases the immunogenicity of the fragment, such as keyhole limpet hemocyanin (as described above). The polyclonal or monoclonal antibodies so produced can be screened using purified recombinant or naturally occurring maspin, or as described above, to select those which form an immunocomplex with maspin specifically.

The antibodies so produced are employed in diagnostic methods for detecting cells, tissues, or biological fluids in which the presence of maspin is decreased relative to normal cells, an indication that the patient has a carcinoma. The sample tested may be a fixed section of a tissue biopsy, a preparation of cells obtained from a suspect tissue, or a sample of biological fluid, such as blood, serum, urine, sweat, tears, cerebrospinal fluid, milk, ductal fluid, or semen. Standard methods of immunoassay may be used, including those described above as well as sandwich ELISA. If the tested cells express no detectable maspin protein in this assay, while normal cells of the same tissue type do express a detectable level of maspin, the tested cells are likely to represent an advanced, metastatic carcinoma. If the tested cells express a decreased but consistently detectable level of maspin, the tested cells are probably from an early stage carcinoma that is not yet metastatic. Where the sample tested is a biological fluid into which maspin would normally be secreted, the fluid may be directly contacted with the anti-maspin antibody, or can be first partially processed (e.g., centrifuged, pre-cleared with other antibodies, dialyzed, or passed over a column) before using the anti-maspin antibody. The amount of immunocomplex formed between the proteins of the sample and the anti-maspin antibody is then determined, and can be compared to a normal control run in parallel, or to a previously-determined standard.

Example 4

In Vivo and in Vitro Assays

The in vivo assay described above, in which tumor growth is measured in severely immunodeficient mice (e.g., nude mice), is useful in a number of applications concerning the present invention. For example, the assay can be used to determine (1) whether or not growth of a given carcinoma is inhibited by treatment either with maspin or an agent which increases the concentration of maspin in the carcinoma cells; or (2) whether or not a given candidate compound, which may be known to increase maspin expression in carcinomas in which maspin expression is down-regulated, can in fact inhibit growth of such carcinomas. The nude mice (or any other severely immunodeficient animal, such as a rat, rabbit, or other mammal) can also be adapted to study the effect of a given treatment on the rate of metastasis of the tumor, using standard methods of in vivo analysis of metastasis.

A second type of assay described above, the in vitro assay of tumor cell invasion through reconstituted basement membrane matrix (e.g., MATRIGEL®), is also generally useful with respect to the present invention. Using this assay, the increase in invasive capacity of a given carcinoma over time, or of a series of carcinomas from different patients, can be correlated with the degree of inhibition of maspin expression in each carcinoma sample. The assay can be used to screen various treatment protocols to determine whether a given maspin-increasing protocol is effective in reducing invasive capacity in a given carcinoma.

Example 5

Assay for Presence of Intact Gene

If expression of the maspin tumor suppressor gene is down-regulated in the cells of a given carcinoma, but the gene remains present and intact in such cells, it is possible that the cells could be treated in a way that stimulates re-expression of the gene and thereby reverses or at least halts the progression of the carcinoma. This strategy would require affirmation that the gene remains intact and therefore available for up-regulation in the particular cancer cells to be treated. A Southern analysis of genomic DNA from the cancer cells and normal cells, such as described above, would provide evidence that the maspin gene in the cancer cells is largely intact. Use of a battery of restriction enzymes would permit a more rigorous analysis of whether changes in the gene sequence had occurred in the cancer cells. One could use as hybridization probe full-length maspin cDNA (SEQ ID NO:1), maspin genomic DNA, or a fragment of either. To obtain maspin genomic DNA, a human genomic DNA library is probed with maspin cDNA (SEQ ID NO:1), using standard techniques such as described in Sambrook et al., Molecular Cloning: A Laboratory Manual (2nd Edition), Cold Spring Harbor Laboratory, Cold Spring Harbor, N.Y. (1989), herein incorporated by reference. The expression control elements of the naturally-occurring maspin gene (e.g., promoters and enhancers usually located 5' to the transcription start site, or within one or more introns, but also possibly in the 3' untranslated region) are of particular interest, since down-regulation of transcription is associated with tumor progression.

Example 6

Screen for and Use of Therapeutic Agents

Carcinoma or other cells in which the endogenous maspin gene is present but down-regulated can be used as a screening tool to identify compounds or treatment strategies which induce re-expression of the maspin gene. Re-expression of other down-regulated candidate tumor suppressor genes has been described: connexin 26, encoding a gap junction protein, by PMA (Lee et al., J. Cell Biol. 118:1213, 1992), and a small calcium binding protein, CAN19, by deoxyazacytidine (Lee et al., Proc. Natl. Acad. Sci. USA 89:2504, 1992). Of particular use in such a screen would be cell lines derived from an appropriate carcinoma, with a control being the same cells transfected with a vector encoding maspin cDNA linked to expression control elements which permit constitutive expression of the cDNA (e.g., the CMV promoter), as described above. However, other cell types with intact but unexpressed maspin genes would also be potentially useful in this screening assay. The cells would be treated in vitro with the candidate compounds, and the amount of maspin expression determined using either a hybridization assay (e.g., Northern analysis) or an immunoassay. The latter could be designed to detect intracellular maspin or secreted maspin, or both. If a given compound is found to stimulate maspin expression in the carcinoma cells, it could then be further tested to see whether treatment with the compound prevents carcinoma growth in the nude mouse model described above. A compound effective both in stimulating maspin expression and in preventing carcinoma growth is a potential therapeutic useful for the treatment of carcinomas down-regulated in maspin expression. Further evaluation of the clinical usefulness of such a compound would follow standard methods of evaluating toxicity and clinical effectiveness of anticancer agents.

Example 7

Treatment with Maspin

As discussed above, increasing the amount of maspin in a carcinoma cell appears to correlate with a decrease in both growth rate and invasive activity of the tumor. Thus, it is expected that treating a patient with maspin, or a biologically active (i.e., protease-inhibiting) fragment of maspin, will help counter the effects of down-regulation of the maspin gene in the patient's carcinoma cells. Since maspin is a secreted protein, it is likely that it exerts its tumor growth-suppressing effect extracellularly. A useful treatment protocol will therefore be a simple method such as intravenous injection of the protein in a pharmaceutically acceptable solution in a dosage of 0.001 to 100 mg/kg/day, with the most beneficial range to be determined using routine pharmacological methods. This protocol has the advantage of potentially reaching all metastases of the tumor. Alternative routes of delivery would also be acceptable, such as intramuscular or subcutaneous injection, injection directly into the tumor site, or implantation of a device containing a slow-release formulation. If it is desired to ensure that the exogenous maspin protein is incorporated into the carcinoma cells themselves, the protein could be incorporated into liposomes or another form of carrier which permits substantial amounts of the protein to pass through the cell membrane. Liposomes would also help protect the protein from proteolytic degradation while in the bloodstream.

Example 8

Genetic Therapy

As disclosed above, an expression vector encoding maspin can be introduced into carcinoma cells, thereby increasing the production of maspin in the transfected cells, and decreasing the in vivo growth rate of tumors derived from these cells. The transfected cells are also shown above to have a decreased invasive character, compared to untransfected controls. This evidence indicates that the maspin DNA of the invention will be useful for genetic therapy to help control carcinomas characterized by down-regulated maspin expression, or to ensure that early-stage carcinomas which have not yet lost the ability to manufacture maspin do not progress through the progressively down-regulated stages. Standard methods of gene therapy may be employed: e.g., as described in Friedmann, *Therapy for Genetic Disease*, T. Friedman (ed.), Oxford Univ. Press, 1991, pp.105–121. Virus or plasmids containing a copy of the maspin cDNA linked to expression control sequences which permit expression in the carcinoma cell would be introduced into the patient, either locally at the site of the tumor or systemically (in order to reach any tumor cells that may have metastasized to other sites). If the transfected DNA encoding maspin is not stably incorporated into the genome of each of the targeted carcinoma cells, the treatment may have to be repeated periodically.

| Cells | Tumor/Site (6 weeks) | Mean Weight-(gram) (10 weeks) |
|---|---|---|
| pCMVneo N1 | 8/10 | 0.74 (7) |
| pCMVneo N2 | 10/10 | 1.77 (6) |
| pCMVmaspin T1 | 8/10 | 1.67 (4) |
| pCMVmaspin T4 | 6/10 | 0.31 (7) |
| pCMVmaspin T5 | 5/10 | 0.35 (7) |
| pCMVmaspin T6 | 8/10 | 0.43 (9) | p = 0.034 (T1–T6)
p = 0.00057 (T4–T6)

TABLE 2

Correlation of maspin sequences with human chromosomes in human-rodent cell hybrids. High molecular weight chromosomal DNAs isolated from parental and hybrid cell lines (obtained from NIGMS as mapping panel 2) were treated with HindIII HundIII, fractionated in 0.8% agarose gels, and transferred to nylon filters. A $^{32}$p-labeled maspin cDNA probe was prepared by oligonucleotide labeling and hybridized in the filters as described (Hagiwara et al., Mol. Cell Biol. 11:2125, 1991).

| Chromosome | 1 | 2 | 3 | 4 | 5 | 6 | 7 | 8 | 9 | 10 | 11 | 12 | 13 | 14 | 15 | 16 | 17 | 18 | 19 | 20 | 21 | 22 | X | Y |
|---|---|---|---|---|---|---|---|---|---|---|---|---|---|---|---|---|---|---|---|---|---|---|---|---|
| Descordancy Ratio | 2/24 | 2/24 | 2/24 | 2/24 | 2/24 | 2/24 | 2/24 | 2/24 | 2/24 | 2/24 | 2/24 | 2/24 | 2/24 | 2/24 | 2/24 | 2/24 | 2/24 | 0/24 | 2/24 | 2/24 | 2/24 | 2/24 | 3/24 | 2/24 |

5,470,970

What is claimed is:

1. A single- or double-stranded isolated DNA encoding a polypeptide having at least 90% sequence identity to maspin (SEQ ID NO:2) wherein said DNA hybridizes under stringent conditions with DNA sequence of SEQ ID NO:1, or the complement of said single stranded DNA.

2. The isolated DNA of claim 1, wherein said DNA comprises the sequence of SEQ ID NO:1, or the complement thereof.

3. A vector comprising the isolated DNA of claim 1.

4. Isolated genomic DNA encoding a polypeptide having at least 90% sequence identity to maspin (SEQ ID NO:2).

5. A single- or double-stranded isolated cDNA encoding a polypeptide having at least 90% sequence identity to maspin (SEQ ID NO:2).

6. An isolated DNA at least 30 nucleotides in length, comprising (a) a strand which hybridizes under stringent conditions to a DNA having the coding sequence of SEQ ID NO:1, (b) the complement thereof, or (c) a double stranded DNA comprising both (a) and (b).

7. A cell transfected with a vector comprising the isolated DNA of claim 6.

8. An isolated DNA at least 40 nucleotides in length, comprising (a) a strand which hybridizes under stringent conditions to a DNA having the coding sequence of SEQ ID NO:1, (b) the complement thereof, or (c) a double stranded DNA comprising both (a) and (b).

9. An isolated DNA consisting of (a) a fragment of at least 30 nucleotides in length of the coding region of SEQ ID NO: 1, or (b) the complement thereof.

10. A single- or double-stranded isolated DNA encoding maspin (SEQ ID NO:2), or the complement of said single-stranded DNA.

11. The isolated DNA of claim 10, wherein said DNA comprises a sequence which hybridizes under stringent conditions with the DNA sequence of SEQ ID NO:1, or the complement thereof.

12. A vector comprising the isolated DNA of claim 10.

13. The vector of claim 12, wherein said vector includes an expression control sequence operably linked to said isolated DNA.

14. A cell transfected with the vector of claim 12.

15. The cell of claim 14, wherein said cell expresses said polypeptide from said vector.

16. A purified preparation of maspin (SEQ ID NO:2).

17. A hybrid polypeptide comprising (1) maspin (SEQ ID NO:2), covalently attached to (2) a second polypeptide.

* * * * *